US011850140B2

(12) United States Patent
Lamson et al.

(10) Patent No.: US 11,850,140 B2
(45) **Date of Patent: *Dec. 26, 2023**

(54) DEVICES, SYSTEMS AND METHODS FOR TREATING BENIGN PROSTATIC HYPERPLASIA AND OTHER CONDITIONS

(71) Applicant: Teleflex Life Sciences Limited, Valletta (MT)

(72) Inventors: Theodore C. Lamson, Pleasanton, CA (US); Floria Cheng, San Francisco, CA (US); Joseph Catanese, III, San Leandro, CA (US)

(73) Assignee: Teleflex Life Sciences Limited, Valletta (MT)

( * ) Notice: Subject to any disclaimer, the term of this patent is extended or adjusted under 35 U.S.C. 154(b) by 365 days.

This patent is subject to a terminal disclaimer.

(21) Appl. No.: 17/224,996

(22) Filed: Apr. 7, 2021

(65) Prior Publication Data

US 2021/0220111 A1 Jul. 22, 2021

Related U.S. Application Data

(63) Continuation of application No. 16/234,282, filed on Dec. 27, 2018, now abandoned, which is a (Continued)

(51) Int. Cl.
*A61F 2/04* (2013.01)
*A61B 17/04* (2006.01)

(Continued)

(52) U.S. Cl.
CPC ............ *A61F 2/04* (2013.01); *A61B 17/0401* (2013.01); *A61B 17/0469* (2013.01); *A61B 17/0482* (2013.01); *A61B 17/0487* (2013.01); *A61B 17/06109* (2013.01); *A61B 17/42* (2013.01); *A61F 2/0022* (2013.01); *A61B 17/00234* (2013.01); *A61B 17/0218* (2013.01); *A61B 17/0467* (2013.01); *A61B 17/3468* (2013.01); *A61B 17/3478* (2013.01);

(Continued)

(58) Field of Classification Search
None
See application file for complete search history.

(56) References Cited

U.S. PATENT DOCUMENTS 659,422 A 10/1900 Shidler
780,392 A 1/1905 Wanamaker et al.

(Continued)

FOREIGN PATENT DOCUMENTS

CA 2477220 11/2007
CN 1697633 A 11/2005

(Continued)

OTHER PUBLICATIONS

Bacharova, O.A., et al. "The Effect of Rhodiolae rosea Extract on Incidence Rate of Superficial Bladder Carcinoma Relapses", Kozin 1995.

(Continued)

*Primary Examiner* — Shaun L David

(74) *Attorney, Agent, or Firm* — Erik T . Nyre; Kenneth E. Levitt

(57) ABSTRACT

Extra-urethral implants and methods of use are disclosed. Implants can treat disorders or diseases of the prostate by, for example, enlarging the lumen of the prostatic urethra.

20 Claims, 12 Drawing Sheets

Related U.S. Application Data continuation of application No. 13/830,811, filed on Mar. 14, 2013, now Pat. No. 10,195,014.

(51) Int. Cl.

| | |
|---|---|
| *A61B 17/06* | (2006.01) |
| *A61B 17/42* | (2006.01) |
| *A61F 2/00* | (2006.01) |
| *A61B 18/00* | (2006.01) |
| *A61B 18/14* | (2006.01) |
| *A61B 18/18* | (2006.01) |
| *A61B 18/20* | (2006.01) |
| *A61B 17/00* | (2006.01) |
| *A61B 17/02* | (2006.01) |
| *A61B 17/34* | (2006.01) |

(52) U.S. Cl.

CPC ........... *A61B 18/14* (2013.01); *A61B 18/1815* (2013.01); *A61B 18/20* (2013.01); *A61B 2017/00022* (2013.01); *A61B 2017/00274* (2013.01); *A61B 2017/00792* (2013.01); *A61B 2017/00796* (2013.01); *A61B 2017/00805* (2013.01); *A61B 2017/0404* (2013.01); *A61B 2017/0409* (2013.01); *A61B 2017/0417* (2013.01); *A61B 2017/0419* (2013.01); *A61B 2017/0451* (2013.01); *A61B 2017/0454* (2013.01); *A61B 2017/0456* (2013.01); *A61B 2017/0458* (2013.01); *A61B 2017/0462* (2013.01); *A61B 2017/0464* (2013.01); *A61B 2017/0488* (2013.01); *A61B 2017/06052* (2013.01); *A61B 2017/06176* (2013.01); *A61B 2018/00547* (2013.01); *A61F 2002/047* (2013.01)

(56) References Cited

U.S. PATENT DOCUMENTS 789,467 A 5/1905 West
2,360,164 A 10/1944 Frank
2,485,531 A 10/1949 William et al.
2,579,192 A 12/1951 Alexander
2,646,298 A 7/1953 Leary
2,697,624 A 12/1954 Thomas et al.
2,734,299 A 2/1956 Masson
2,825,592 A 3/1958 Mckenzie
3,326,586 A 6/1967 Frost et al.
3,470,834 A 10/1969 Bone
3,521,918 A 7/1970 Hammond
3,541,591 A 11/1970 Hoegerman
3,664,345 A 5/1972 Dabbs et al.
3,713,680 A 1/1973 Pagano
3,716,058 A 2/1973 Tanner
3,756,638 A 9/1973 Stockberger
3,873,140 A 3/1975 Bloch
3,875,648 A 4/1975 Bone
3,886,933 A 6/1975 Mori et al.
3,931,667 A 1/1976 Merser et al.
3,976,079 A 8/1976 Samuels et al.
4,006,747 A 2/1977 Kronenthal et al.
4,137,920 A 2/1979 Bonnet
4,164,225 A 8/1979 Johnson et al.
4,210,148 A 7/1980 Stivala
4,235,238 A 11/1980 Ogiu et al.
4,291,698 A 9/1981 Fuchs et al.
4,409,974 A 10/1983 Freedland
4,419,094 A 12/1983 Patel
4,452,236 A 6/1984 Utsugi
4,493,323 A 1/1985 Albright et al.
4,513,746 A 4/1985 Aranyi et al.
4,621,640 A 11/1986 Mulhollan et al.
4,655,771 A 4/1987 Wallsten
4,657,461 A 4/1987 Smith
4,669,473 A 6/1987 Richards et al.
4,705,040 A 11/1987 Mueller et al.
4,714,281 A 12/1987 Peck
4,738,255 A 4/1988 Goble et al.
4,741,330 A 5/1988 Hayhurst
4,744,364 A 5/1988 Kensey
4,750,492 A 6/1988 Jacobs
4,762,128 A 8/1988 Rosenbluth
4,823,794 A 4/1989 Pierce
4,863,439 A 9/1989 Sanderson
4,893,623 A 1/1990 Rosenbluth
4,899,743 A 2/1990 Nicholson et al.
4,926,860 A 5/1990 Stice et al.
4,935,028 A 6/1990 Drews
4,946,468 A 8/1990 Li
4,955,859 A 9/1990 Zilber
4,955,913 A 9/1990 Robinson
4,968,315 A 11/1990 Gatturna
4,994,066 A 2/1991 Voss
5,002,550 A 3/1991 Li
5,019,032 A 5/1991 Robertson
5,041,129 A 8/1991 Hayhurst et al.
5,046,513 A 9/1991 Gatturna et al.
5,053,046 A 10/1991 Janese
5,078,731 A 1/1992 Hayhurst
5,080,660 A 1/1992 Buelna
5,098,374 A 3/1992 Othel-Jacobsen et al.
5,100,421 A 3/1992 Christoudias
5,123,914 A 6/1992 Cope
5,127,393 A 7/1992 McFarlin et al.
5,129,912 A 7/1992 Noda et al.
5,133,713 A 7/1992 Huang et al.
5,159,925 A 11/1992 Neuwirth et al.
5,160,339 A 11/1992 Chen et al.
5,163,960 A 11/1992 Bonutti
5,167,614 A 12/1992 Tessmann et al.
5,192,303 A 3/1993 Gatturna et al.
5,203,787 A 4/1993 Noblitt et al.
5,207,672 A 5/1993 Roth et al.
5,217,470 A 6/1993 Weston
5,217,486 A 6/1993 Rice et al.
5,234,454 A 8/1993 Bangs
5,236,445 A 8/1993 Hayhurst et al.
5,237,984 A 8/1993 Williams et al.
5,254,126 A 10/1993 Filipi et al.
5,258,015 A 11/1993 Li et al.
5,267,960 A 12/1993 Hayman et al.
5,269,802 A 12/1993 Garber
5,269,809 A 12/1993 Hayhurst et al.
5,300,099 A 4/1994 Rudie
5,306,280 A 4/1994 Bregen et al.
5,322,501 A 6/1994 Mahmud-Durrani
5,330,488 A 7/1994 Goldrath
5,334,200 A 8/1994 Johnson
5,336,240 A 8/1994 Metzler et al.
5,350,399 A 9/1994 Erlebacher et al.
5,354,271 A 10/1994 Voda
5,358,511 A 10/1994 Gatturna et al.
5,364,408 A 11/1994 Gordon
5,366,490 A 11/1994 Edwards et al.
5,368,599 A 11/1994 Hirsch et al.
5,370,646 A 12/1994 Reese et al.
5,370,661 A 12/1994 Branch
5,372,600 A 12/1994 Beyar et al.
5,380,334 A 1/1995 Torrie et al.
5,391,182 A 2/1995 Chin
5,403,348 A 4/1995 Bonutti
5,405,352 A 4/1995 Weston
5,409,453 A 4/1995 Lundquist et al.
5,411,520 A 5/1995 Nash et al.
5,417,691 A 5/1995 Hayhurst
5,435,805 A 7/1995 Edwards et al.
5,441,485 A 8/1995 Peters
5,458,612 A 10/1995 Chin
5,464,416 A 11/1995 Steckel
5,470,308 A 11/1995 Edwards et al.
5,470,337 A 11/1995 Moss
5,472,446 A 12/1995 Torre

(56) References Cited

U.S. PATENT DOCUMENTS 5,480,406 A 1/1996 Nolan et al.
5,499,994 A 3/1996 Tihon et al.
5,501,690 A 3/1996 Measamer et al.
5,507,754 A 4/1996 Green et al.
5,522,846 A 6/1996 Bonutti
5,531,759 A 7/1996 Kensey et al.
5,531,763 A 7/1996 Mastri et al.
5,534,012 A 7/1996 Bonutti
5,536,240 A 7/1996 Edwards et al.
5,540,655 A 7/1996 Edwards et al.
5,540,701 A 7/1996 Sharkey et al.
5,540,704 A 7/1996 Gordon et al.
5,542,594 A 8/1996 McKean et al.
5,545,171 A 8/1996 Sharkey et al.
5,545,178 A 8/1996 Kensey et al.
5,549,631 A 8/1996 Bonutti
5,550,172 A 8/1996 Regula et al.
5,554,162 A 9/1996 DeLange
5,554,171 A 9/1996 Gatturna et al.
5,562,688 A 10/1996 Riza
5,562,689 A 10/1996 Green et al.
5,569,305 A 10/1996 Bonutti
5,571,104 A 11/1996 Li
5,573,540 A 11/1996 Yoon
5,578,044 A 11/1996 Gordon et al.
5,591,177 A 1/1997 Lehrer
5,591,179 A 1/1997 Edelstein
5,593,421 A 1/1997 Bauer
5,611,515 A 3/1997 Benderev et al.
5,620,461 A 4/1997 Moer et al.
5,626,614 A 5/1997 Hart
5,630,824 A 5/1997 Hart
5,643,321 A 7/1997 McDevitt
5,647,836 A 7/1997 Blake et al.
5,653,373 A 8/1997 Green et al.
5,665,109 A 9/1997 Yoon
5,667,486 A 9/1997 Mikulich et al.
5,667,488 A 9/1997 Lundquist et al.
5,667,522 A 9/1997 Flomenblit et al.
5,669,917 A 9/1997 Sauer et al.
5,672,171 A 9/1997 Andrus et al.
5,690,649 A 11/1997 Li
5,690,677 A 11/1997 Schmieding et al.
5,697,950 A 12/1997 Fucci et al.
5,707,394 A 1/1998 Miller et al.
5,716,368 A 2/1998 Torre et al.
5,718,717 A 2/1998 Bonutti
5,725,556 A 3/1998 Moser et al.
5,725,557 A 3/1998 Gatturna et al.
5,733,306 A 3/1998 Bonutti
5,741,276 A 4/1998 Poloyko et al.
5,746,753 A 5/1998 Sullivan et al.
5,749,846 A 5/1998 Edwards et al.
5,749,889 A 5/1998 Bacich et al.
5,752,963 A 5/1998 Allard et al.
5,775,328 A 7/1998 Lowe et al.
5,782,862 A 7/1998 Bonutti
5,782,864 A 7/1998 Lizardi
5,791,022 A 8/1998 Bohman
5,800,445 A 9/1998 Ratcliff et al.
5,807,403 A 9/1998 Beyar et al.
5,810,848 A 9/1998 Hayhurst
5,810,853 A 9/1998 Yoon
5,814,072 A 9/1998 Bonutti
5,830,179 A 11/1998 Mikus et al.
5,830,221 A 11/1998 Stein et al.
5,845,645 A 12/1998 Bonutti
5,846,254 A 12/1998 Schulze et al.
5,861,002 A 1/1999 Desai
5,868,762 A 2/1999 Cragg et al.
5,873,891 A 2/1999 Sohn
5,879,357 A 3/1999 Heaton et al.
5,897,574 A 4/1999 Bonutti
5,899,911 A 5/1999 Carter
5,899,921 A 5/1999 Caspari et al.
5,904,679 A 5/1999 Clayman
5,904,696 A 5/1999 Rosenman
5,908,428 A 6/1999 Scirica et al.
5,908,447 A 6/1999 Schroeppel et al.
5,919,198 A 7/1999 Graves et al.
5,919,202 A 7/1999 Yoon
5,921,982 A 7/1999 Lesh et al.
5,921,986 A 7/1999 Bonutti
5,928,252 A 7/1999 Steadman et al.
5,931,844 A 8/1999 Thompson et al.
5,941,439 A 8/1999 Kammerer et al.
5,944,739 A 8/1999 Zlock et al.
5,948,000 A 9/1999 Larsen et al.
5,948,001 A 9/1999 Larsen
5,948,002 A 9/1999 Bonutti
5,954,057 A 9/1999 Li
5,954,747 A 9/1999 Clark
5,964,732 A 10/1999 Willard
5,971,447 A 10/1999 Steck
5,971,967 A 10/1999 Willard
6,010,514 A 1/2000 Burney et al.
6,011,525 A 1/2000 Piole
6,015,428 A 1/2000 Pagedas
6,024,751 A 2/2000 Lovato et al.
6,030,393 A 2/2000 Corlew
6,033,413 A 3/2000 Mikus et al.
6,033,430 A 3/2000 Bonutti
6,036,701 A 3/2000 Rosenman
6,048,351 A 4/2000 Gordon et al.
6,053,908 A 4/2000 Crainich et al.
6,053,935 A 4/2000 Brenneman et al.
6,056,722 A 5/2000 Jayaraman
6,056,772 A 5/2000 Bonutti
6,066,160 A 5/2000 Colvin et al.
6,068,648 A 5/2000 Cole et al.
6,080,167 A 6/2000 Lyell
6,086,608 A 7/2000 Ek et al.
6,110,183 A 8/2000 Cope
6,117,133 A 9/2000 Zappala
6,117,160 A 9/2000 Bonutti
6,117,161 A 9/2000 Li et al.
6,120,539 A 9/2000 Eldridge et al.
6,132,438 A 10/2000 Fleischman et al.
6,139,555 A 10/2000 Hart et al.
RE36,974 E 11/2000 Bonutti
6,143,006 A 11/2000 Chan
6,152,935 A 11/2000 Kammerer et al.
6,156,044 A 12/2000 Kammerer et al.
6,156,049 A 12/2000 Lovato et al.
6,159,207 A 12/2000 Yoon
6,159,234 A 12/2000 Bonutti et al.
6,193,714 B1 2/2001 McGaffigan et al.
6,200,329 B1 3/2001 Fung et al.
6,203,565 B1 3/2001 Bonutti et al.
6,206,895 B1 3/2001 Levinson
6,206,907 B1 3/2001 Marino et al.
6,228,096 B1 5/2001 Marchand
6,235,024 B1 5/2001 Tu
6,258,124 B1 7/2001 Darois et al.
6,261,302 B1 7/2001 Voegele et al.
6,261,320 B1 7/2001 Tam et al.
6,270,530 B1 8/2001 Eldridge et al.
6,280,441 B1 8/2001 Ryan
6,280,460 B1 8/2001 Bolduc et al.
6,287,317 B1 9/2001 Makower et al.
6,290,711 B1 9/2001 Caspari et al.
6,295,990 B1 10/2001 Lewis et al.
6,306,158 B1 10/2001 Bartlett
6,312,448 B1 11/2001 Bonutti
6,319,263 B1 11/2001 Levinson
6,322,112 B1 11/2001 Duncan
6,332,889 B1 12/2001 Sancoff et al.
6,382,214 B1 5/2002 Raz et al.
6,387,041 B1 5/2002 Harari et al.
6,398,795 B1 6/2002 McAlister et al.
6,398,796 B2 6/2002 Levinson
6,425,900 B1 7/2002 Knodel et al.
6,425,919 B1 7/2002 Lambrecht
6,428,538 B1 8/2002 Blewett et al.

(56) References Cited

U.S. PATENT DOCUMENTS 6,428,562 B2 8/2002 Bonutti
6,436,107 B1 8/2002 Wang et al.
6,461,355 B2 10/2002 Svejkovsky et al.
6,482,235 B1 11/2002 Lambrecht et al.
6,488,691 B1 12/2002 Carroll et al.
6,491,672 B2 12/2002 Slepian et al.
6,491,707 B2 12/2002 Makower et al.
6,494,888 B1 12/2002 Laufer et al.
6,500,184 B1 12/2002 Chan et al.
6,500,195 B2 12/2002 Bonutti
6,506,190 B1 1/2003 Walshe
6,506,196 B1 1/2003 Laufer
6,514,247 B1 2/2003 McGaffigan et al.
6,517,569 B2 2/2003 Mikus et al.
6,527,702 B2 3/2003 Whalen et al.
6,527,794 B1 3/2003 McDevitt et al.
6,530,932 B1 3/2003 Swayze et al.
6,530,933 B1 3/2003 Yeung et al.
6,533,796 B1 3/2003 Sauer et al.
6,544,230 B1 4/2003 Flaherty et al.
6,547,725 B1 4/2003 Paolitto et al.
6,551,328 B2 4/2003 Kortenbach
6,551,333 B2 4/2003 Kuhns et al.
6,565,578 B1 5/2003 Peifer et al.
6,569,187 B1 5/2003 Bonutti et al.
6,572,626 B1 6/2003 Knodel et al.
6,572,635 B1 6/2003 Bonutti
6,572,653 B1 6/2003 Simonson
6,582,453 B1 6/2003 Tran et al.
6,592,609 B1 7/2003 Bonutti
6,595,911 B2 7/2003 LoVuolo
6,596,013 B2 7/2003 Yang et al.
6,599,311 B1 7/2003 Biggs et al.
6,626,913 B1 9/2003 McKinnon et al.
6,626,916 B1 9/2003 Yeung et al.
6,626,919 B1 9/2003 Swanstrom
6,629,534 B1 10/2003 Goar et al.
6,638,275 B1 10/2003 McGaffigan et al.
6,641,524 B2 11/2003 Kovac
6,641,592 B1 11/2003 Sauer et al.
6,656,182 B1 12/2003 Hayhurst
6,660,008 B1 12/2003 Foerster et al.
6,660,023 B2 12/2003 McDevitt et al.
6,663,589 B1 12/2003 Halevy
6,663,633 B1 12/2003 Pierson
6,663,639 B1 12/2003 Laufer et al.
6,699,263 B2 3/2004 Cope
6,702,846 B2 3/2004 Mikus et al.
6,706,047 B2 3/2004 Trout et al.
6,709,493 B2 3/2004 DeGuiseppi et al.
6,715,804 B2 4/2004 Beers
6,716,252 B2 4/2004 Lazarovitz et al.
6,719,709 B2 4/2004 Whalen et al.
6,730,112 B2 5/2004 Levinson
6,736,823 B2 5/2004 Darois et al.
6,736,854 B2 5/2004 Vadurro et al.
6,740,098 B2 5/2004 Abrams et al.
6,767,037 B2 7/2004 Wenstrom
6,770,076 B2 8/2004 Foerster
6,770,101 B2 8/2004 Desmond, III et al.
6,773,438 B1 8/2004 Knodel et al.
6,773,441 B1 8/2004 Laufer et al.
6,790,213 B2 9/2004 Cherok et al.
6,790,223 B2 9/2004 Reever
6,802,838 B2 10/2004 Loeb et al.
6,802,846 B2 10/2004 Hauschild et al.
6,821,282 B2 11/2004 Perry et al.
6,821,285 B2 11/2004 Laufer et al.
6,821,291 B2 11/2004 Bolea et al.
6,835,200 B2 12/2004 Laufer et al.
6,905,475 B2 6/2005 Hauschild et al.
6,908,473 B2 6/2005 Skiba et al.
6,921,361 B2 7/2005 Suzuki et al.
6,926,732 B2 8/2005 Derus et al.
6,951,565 B2 10/2005 Keane et al.
6,986,775 B2 1/2006 Morales et al.
6,986,784 B1 1/2006 Weiser et al.
6,988,983 B2 1/2006 Connors et al.
6,991,596 B2 1/2006 Whalen et al.
6,991,647 B2 1/2006 Jadhav
6,997,940 B2 2/2006 Bonutti
7,001,327 B2 2/2006 Whalen et al.
7,004,965 B2 2/2006 Gross
7,008,381 B2 3/2006 Janssens
7,011,688 B2 3/2006 Gryska et al.
7,015,253 B2 3/2006 Escandon et al.
7,041,111 B2 5/2006 Chu
7,048,698 B2 5/2006 Whalen et al.
7,048,747 B2 5/2006 Arcia et al.
7,060,077 B2 6/2006 Gordon et al.
7,063,715 B2 6/2006 Onuki et al.
7,065,325 B2 6/2006 Zegelin et al.
7,081,126 B2 7/2006 McDevitt et al.
7,083,638 B2 8/2006 Foerster
7,087,073 B2 8/2006 Bonutti
7,089,064 B2 8/2006 Manker et al.
7,090,690 B2 8/2006 Foerster et al.
7,093,601 B2 8/2006 Manker et al.
7,096,301 B2 8/2006 Beaudoin et al.
7,104,949 B2 9/2006 Anderson et al.
7,105,004 B2 9/2006 DiCesare et al.
7,108,655 B2 9/2006 Whalen et al.
7,112,226 B2 9/2006 Gellman
7,141,038 B2 11/2006 Whalen et al.
7,153,314 B2 12/2006 Laufer et al.
7,179,225 B2 2/2007 Shluzas et al.
7,226,558 B2 6/2007 Nieman et al.
7,232,448 B2 6/2007 Battles et al.
7,255,675 B2 8/2007 Gertner et al.
7,261,709 B2 8/2007 Swoyer et al.
7,261,710 B2 8/2007 Elmouelhi et al.
7,282,020 B2 10/2007 Kaplan
7,288,063 B2 10/2007 Petros et al.
7,303,108 B2 12/2007 Shelton
7,320,701 B2 1/2008 Haut et al.
7,322,974 B2 1/2008 Swoyer et al.
7,326,221 B2 2/2008 Sakamoto et al.
7,334,822 B1 2/2008 Hines
7,335,197 B2 2/2008 Sage et al.
7,340,300 B2 3/2008 Christopherson et al.
7,399,304 B2 7/2008 Gambale et al.
7,402,166 B2 7/2008 Feigl
7,416,554 B2 8/2008 Lam et al.
7,417,175 B2 8/2008 Oda et al.
7,437,194 B2 10/2008 Skwarek et al.
7,463,934 B2 12/2008 Tronnes et al.
7,470,228 B2 12/2008 Connors et al.
7,481,771 B2 1/2009 Fonseca et al.
7,485,124 B2 2/2009 Kuhns et al.
7,553,317 B2 6/2009 William et al.
7,608,108 B2 10/2009 Bhatnagar et al.
7,632,297 B2 12/2009 Gross
7,645,286 B2 1/2010 Catanese et al.
7,658,311 B2 2/2010 Boudreaux
7,666,197 B2 2/2010 Orban
7,674,275 B2 3/2010 Martin et al.
7,682,374 B2 3/2010 Foerster et al.
7,695,494 B2 4/2010 Foerster
7,704,261 B2 4/2010 Sakamoto et al.
7,727,248 B2 6/2010 Smith et al.
7,731,725 B2 6/2010 Gadberry et al.
7,736,374 B2 6/2010 Vaughan et al.
7,758,594 B2 7/2010 Lamson et al.
7,766,923 B2 8/2010 Catanese et al.
7,766,939 B2 8/2010 Yeung et al.
7,780,682 B2 8/2010 Catanese et al.
7,780,687 B2 8/2010 Heinrich et al.
7,794,494 B2 9/2010 Sahatjian et al.
7,815,655 B2 10/2010 Catanese et al.
7,850,712 B2 12/2010 Conlon et al.
7,862,584 B2 1/2011 Lyons et al.
7,887,551 B2 2/2011 Bojarski et al.
7,896,891 B2 3/2011 Catanese et al.
7,905,889 B2 3/2011 Catanese et al.

(56) References Cited

U.S. PATENT DOCUMENTS

| | | | |
|---|---|---|---|
| 7,905,904 | B2 | 3/2011 | Stone et al. |
| 7,909,836 | B2 | 3/2011 | McLean et al. |
| 7,914,542 | B2 | 3/2011 | Lamson et al. |
| 7,922,645 | B2 | 4/2011 | Kaplan |
| 7,951,158 | B2 | 5/2011 | Catanese et al. |
| 8,007,503 | B2 | 8/2011 | Catanese et al. |
| 8,043,309 | B2 | 10/2011 | Catanese et al. |
| 8,114,070 | B2 | 2/2012 | Rubinsky et al. |
| 8,145,321 | B2 | 3/2012 | Gross |
| 8,152,804 | B2 | 4/2012 | Elmouelhi et al. |
| 8,157,815 | B2 | 4/2012 | Catanese et al. |
| 8,162,960 | B2 | 4/2012 | Manzo |
| 8,167,830 | B2 | 5/2012 | Noriega |
| 8,211,118 | B2 | 7/2012 | Catanese et al. |
| 8,216,254 | B2 | 7/2012 | McLean et al. |
| 8,236,011 | B2 | 8/2012 | Harris et al. |
| 8,251,985 | B2 | 8/2012 | Hoey et al. |
| 8,273,079 | B2 | 9/2012 | Hoey et al. |
| 8,298,132 | B2 | 10/2012 | Connors et al. |
| 8,303,604 | B2 | 11/2012 | Stone et al. |
| 8,308,765 | B2 | 11/2012 | Saadat et al. |
| 8,333,776 | B2 | 12/2012 | Cheng et al. |
| 8,343,187 | B2 | 1/2013 | Lamson et al. |
| 8,361,112 | B2 | 1/2013 | Kempton et al. |
| 8,372,065 | B2 | 2/2013 | Hoey et al. |
| 8,388,611 | B2 | 3/2013 | Shadduck et al. |
| 8,388,653 | B2 | 3/2013 | Nobis et al. |
| 8,394,110 | B2 | 3/2013 | Catanese et al. |
| 8,394,113 | B2 | 3/2013 | Wei et al. |
| 8,419,723 | B2 | 4/2013 | Shadduck et al. |
| 8,425,535 | B2 | 4/2013 | McLean et al. |
| 8,444,657 | B2 | 5/2013 | Saadat et al. |
| 8,454,655 | B2 | 6/2013 | Yeung et al. |
| 8,465,551 | B1 | 6/2013 | Wijay et al. |
| 8,480,686 | B2 | 7/2013 | Bakos et al. |
| 8,491,606 | B2 | 7/2013 | Tong et al. |
| 8,496,684 | B2 | 7/2013 | Crainich et al. |
| 8,521,257 | B2 | 8/2013 | Whitcomb et al. |
| 8,529,584 | B2 | 9/2013 | Catanese et al. |
| 8,529,588 | B2 | 9/2013 | Ahlberg et al. |
| 8,562,646 | B2 | 10/2013 | Gellman et al. |
| 8,585,692 | B2 | 11/2013 | Shadduck et al. |
| 8,603,106 | B2 | 12/2013 | Catanese et al. |
| 8,603,123 | B2 | 12/2013 | Todd |
| 8,603,187 | B2 | 12/2013 | Kilemnick et al. |
| 8,628,542 | B2 | 1/2014 | Merrick et al. |
| 8,663,243 | B2 | 3/2014 | Lamson et al. |
| 8,668,705 | B2 | 3/2014 | Johnston et al. |
| 8,683,895 | B2 | 4/2014 | Nash |
| 8,715,239 | B2 | 5/2014 | Lamson et al. |
| 8,715,298 | B2 | 5/2014 | Catanese et al. |
| 8,734,469 | B2 | 5/2014 | Pribanic et al. |
| 8,790,356 | B2 | 7/2014 | Darois et al. |
| 8,801,702 | B2 | 8/2014 | Hoey et al. |
| 8,808,363 | B2 | 8/2014 | Perry et al. |
| 8,814,856 | B2 | 8/2014 | Elmouelhi et al. |
| 8,828,035 | B2 | 9/2014 | Kim |
| 8,834,458 | B2 | 9/2014 | Neuberger et al. |
| 8,880,195 | B2 | 11/2014 | Azure |
| 8,900,293 | B2 | 12/2014 | Forbes et al. |
| 8,920,437 | B2 | 12/2014 | Harris et al. |
| 8,926,494 | B1 | 1/2015 | Cook et al. |
| 8,945,114 | B2 | 2/2015 | Elmouelhi et al. |
| 9,034,001 | B2 | 5/2015 | Cheng et al. |
| 9,039,740 | B2 | 5/2015 | Wales et al. |
| 9,089,320 | B2 | 7/2015 | Spivey et al. |
| 9,150,817 | B2 | 10/2015 | Furihata et al. |
| 9,179,991 | B2 | 11/2015 | Gozzi et al. |
| 9,204,922 | B2 | 12/2015 | Hooven |
| 9,211,155 | B2 | 12/2015 | Fruland et al. |
| 9,220,874 | B2 | 12/2015 | Pillai et al. |
| 9,272,140 | B2 | 3/2016 | Gerber |
| 9,277,914 | B2 | 3/2016 | Wales et al. |
| 9,345,507 | B2 | 5/2016 | Hoey et al. |
| 9,345,867 | B2 | 5/2016 | Browning |
| 9,393,007 | B2 | 7/2016 | Darois et al. |
| 9,439,643 | B2 | 9/2016 | Darois et al. |
| 9,459,751 | B2 | 10/2016 | Weaver et al. |
| 9,526,555 | B2 | 12/2016 | Hoey et al. |
| 9,549,739 | B2 | 1/2017 | Catanese et al. |
| 9,561,025 | B2 | 2/2017 | Stone et al. |
| 9,592,044 | B2 | 3/2017 | Weir et al. |
| 9,597,145 | B2 | 3/2017 | Nelson et al. |
| 9,668,803 | B2 | 6/2017 | Bhushan et al. |
| 9,675,373 | B2 | 6/2017 | Todd |
| 9,750,492 | B2 | 9/2017 | Ziniti et al. |
| 9,931,192 | B2 | 4/2018 | McLean et al. |
| 10,130,353 | B2 | 11/2018 | Catanese et al. |
| 10,195,014 | B2 | 2/2019 | Lamson et al. |
| 10,702,261 | B2 | 7/2020 | Stiggelbout |
| 10,912,637 | B2 | 2/2021 | Lamson et al. |
| 11,331,093 | B2 | 5/2022 | Catanese et al. |
| 11,504,149 | B2 | 11/2022 | Merrick et al. |
| 11,672,520 | B2 | 6/2023 | Lamson et al. |
| 2001/0041916 | A1 | 11/2001 | Bonutti |
| 2001/0044639 | A1 | 11/2001 | Levinson |
| 2002/0049453 | A1 | 4/2002 | Nobles et al. |
| 2002/0095064 | A1 | 7/2002 | Beyar |
| 2002/0095154 | A1 | 7/2002 | Atkinson et al. |
| 2002/0107540 | A1 | 8/2002 | Whalen et al. |
| 2002/0128684 | A1 | 9/2002 | Foerster |
| 2002/0151967 | A1 | 10/2002 | Mikus et al. |
| 2002/0161382 | A1 | 10/2002 | Neisz et al. |
| 2002/0177866 | A1 | 11/2002 | Weikel et al. |
| 2002/0183740 | A1 | 12/2002 | Edwards et al. |
| 2002/0193809 | A1 | 12/2002 | Meade et al. |
| 2003/0023248 | A1 | 1/2003 | Parodi |
| 2003/0040803 | A1 | 2/2003 | Rioux et al. |
| 2003/0060819 | A1 | 3/2003 | McGovern et al. |
| 2003/0078601 | A1 | 4/2003 | Shikhman et al. |
| 2003/0109769 | A1 | 6/2003 | Lowery et al. |
| 2003/0120309 | A1 | 6/2003 | Colleran et al. |
| 2003/0130575 | A1 | 7/2003 | Desai |
| 2003/0144570 | A1 | 7/2003 | Hunter et al. |
| 2003/0176883 | A1 | 9/2003 | Sauer et al. |
| 2003/0191497 | A1 | 10/2003 | Cope |
| 2003/0199860 | A1 | 10/2003 | Loeb et al. |
| 2003/0204195 | A1 | 10/2003 | Keane et al. |
| 2003/0229263 | A1 | 12/2003 | Connors et al. |
| 2003/0236535 | A1 | 12/2003 | Onuki et al. |
| 2004/0010301 | A1 | 1/2004 | Kindlein et al. |
| 2004/0030217 | A1 | 2/2004 | Yeung et al. |
| 2004/0043052 | A1 | 3/2004 | Hunter et al. |
| 2004/0044350 | A1 | 3/2004 | Martin et al. |
| 2004/0078046 | A1 | 4/2004 | Barzell et al. |
| 2004/0122456 | A1 | 6/2004 | Saadat et al. |
| 2004/0122474 | A1 | 6/2004 | Gellman et al. |
| 2004/0143343 | A1 | 7/2004 | Grocela |
| 2004/0147958 | A1 | 7/2004 | Lam et al. |
| 2004/0162568 | A1 | 8/2004 | Saadat et al. |
| 2004/0167635 | A1 | 8/2004 | Yachia et al. |
| 2004/0172046 | A1 | 9/2004 | Hlavka et al. |
| 2004/0181235 | A1 | 9/2004 | Daignault et al. |
| 2004/0193191 | A1 | 9/2004 | Starksen et al. |
| 2004/0193194 | A1 | 9/2004 | Laufer et al. |
| 2004/0193196 | A1 | 9/2004 | Appling et al. |
| 2004/0194790 | A1 | 10/2004 | Laufer et al. |
| 2004/0215179 | A1 | 10/2004 | Swoyer et al. |
| 2004/0215181 | A1 | 10/2004 | Christopherson et al. |
| 2004/0225305 | A1 | 11/2004 | Ewers et al. |
| 2004/0230316 | A1 | 11/2004 | Cioanta et al. |
| 2004/0243178 | A1 | 12/2004 | Haut et al. |
| 2004/0243179 | A1 | 12/2004 | Foerster |
| 2004/0243180 | A1 | 12/2004 | Donnelly et al. |
| 2004/0243227 | A1 | 12/2004 | Starksen et al. |
| 2004/0260345 | A1 | 12/2004 | Foerster |
| 2005/0010203 | A1 | 1/2005 | Edwards et al. |
| 2005/0013805 | A1 | 1/2005 | Tavori |
| 2005/0033403 | A1 | 2/2005 | Ward et al. |
| 2005/0055087 | A1 | 3/2005 | Starksen |
| 2005/0059929 | A1 | 3/2005 | Bolmsjo et al. |
| 2005/0065550 | A1 | 3/2005 | Starksen et al. |
| 2005/0101982 | A1 | 5/2005 | Ravenscroft et al. |
| 2005/0107811 | A1 | 5/2005 | Starksen et al. |

(56) References Cited

U.S. PATENT DOCUMENTS

2005/0107812 A1 5/2005 Starksen et al.
2005/0137716 A1 6/2005 Gross
2005/0154401 A1 7/2005 Weldon et al.
2005/0165272 A1 7/2005 Okada et al.
2005/0171522 A1 8/2005 Christopherson
2005/0177181 A1 8/2005 Kagan et al.
2005/0192652 A1 9/2005 Cioanta et al.
2005/0203344 A1 9/2005 Orban et al.
2005/0203550 A1 9/2005 Laufer et al.
2005/0216040 A1 9/2005 Gertner et al.
2005/0216078 A1 9/2005 Starksen et al.
2005/0222557 A1 10/2005 Baxter et al.
2005/0251157 A1 11/2005 Saadat et al.
2005/0251159 A1 11/2005 Ewers et al.
2005/0251177 A1 11/2005 Saadat et al.
2005/0251206 A1 11/2005 Maahs et al.
2005/0256530 A1 11/2005 Petros
2005/0267405 A1 12/2005 Shah
2005/0273138 A1 12/2005 To et al.
2005/0283189 A1 12/2005 Rosenblatt
2005/0288694 A1 12/2005 Solomon
2006/0004410 A1 1/2006 Nobis et al.
2006/0020276 A1 1/2006 Saadat et al.
2006/0020327 A1 1/2006 Lashinski et al.
2006/0025750 A1 2/2006 Starksen et al.
2006/0025784 A1 2/2006 Starksen et al.
2006/0025789 A1 2/2006 Laufer et al.
2006/0025819 A1 2/2006 Nobis et al.
2006/0026750 A1 2/2006 Ballance
2006/0030884 A1 2/2006 Yeung et al.
2006/0058817 A1 3/2006 Starksen et al.
2006/0079880 A1 4/2006 Sage et al.
2006/0079881 A1 4/2006 Christopherson et al.
2006/0089636 A1 4/2006 Christopherson et al.
2006/0089646 A1 4/2006 Bonutti
2006/0095058 A1 5/2006 Sivan et al.
2006/0167477 A1 7/2006 Arcia et al.
2006/0167533 A1 7/2006 Spraker et al.
2006/0178680 A1 8/2006 Nelson et al.
2006/0189940 A1 8/2006 Kirsch
2006/0195008 A1 8/2006 Whalen et al.
2006/0199996 A1 9/2006 Caraballo et al.
2006/0241694 A1 10/2006 Cerundolo
2006/0265042 A1 11/2006 Catanese et al.
2006/0271032 A1 11/2006 Chin et al.
2006/0276481 A1 12/2006 Evrard et al.
2006/0276871 A1 12/2006 Lamson et al.
2006/0282081 A1 12/2006 Fanton et al.
2007/0049929 A1 3/2007 Catanese et al.
2007/0049970 A1 3/2007 Belef et al.
2007/0060931 A1 3/2007 Hamilton et al.
2007/0073322 A1 3/2007 Mikkaichi et al.
2007/0073342 A1 3/2007 Stone et al.
2007/0088362 A1 4/2007 Bonutti et al.
2007/0100421 A1 5/2007 Griffin
2007/0112385 A1 5/2007 Conlon
2007/0142846 A1 6/2007 Catanese et al.
2007/0173888 A1 7/2007 Gertner et al.
2007/0179491 A1 8/2007 Kratoska et al.
2007/0179496 A1 8/2007 Swoyer et al.
2007/0198038 A1 8/2007 Cohen et al.
2007/0260259 A1 11/2007 Fanton et al.
2008/0009888 A1 1/2008 Ewers et al.
2008/0021445 A1 1/2008 Elmouelhi et al.
2008/0021485 A1 1/2008 Catanese et al.
2008/0033458 A1 2/2008 McLean et al.
2008/0033488 A1 2/2008 Catanese et al.
2008/0039833 A1 2/2008 Catanese et al.
2008/0039872 A1 2/2008 Catanese et al.
2008/0039874 A1 2/2008 Catanese et al.
2008/0039875 A1 2/2008 Catanese et al.
2008/0039893 A1 2/2008 McLean et al.
2008/0039894 A1 2/2008 Catanese et al.
2008/0039921 A1 2/2008 Wallsten et al.
2008/0045978 A1 2/2008 Kuhns et al.
2008/0051810 A1 2/2008 To et al.
2008/0058710 A1 3/2008 Wilk
2008/0065120 A1 3/2008 Zannis et al.
2008/0082113 A1 4/2008 Bishop et al.
2008/0086172 A1 4/2008 Martin et al.
2008/0091220 A1 4/2008 Chu
2008/0091237 A1 4/2008 Schwartz et al.
2008/0119874 A1 5/2008 Merves
2008/0154378 A1 6/2008 Pelo
2008/0161852 A1 7/2008 Kaiser et al.
2008/0195145 A1 8/2008 Bonutti et al.
2008/0208220 A1 8/2008 Shiono et al.
2008/0221388 A1 9/2008 Seibel et al.
2008/0228202 A1 9/2008 Cropper et al.
2008/0262424 A1 10/2008 Hooft
2008/0269737 A1 10/2008 Elmouelhi et al.
2009/0012537 A1 1/2009 Green
2009/0018553 A1 1/2009 McLean et al.
2009/0060977 A1 3/2009 Lamson et al.
2009/0112234 A1 4/2009 Crainich et al.
2009/0112537 A1 4/2009 Okumura
2009/0118762 A1 5/2009 Crainch et al.
2009/0163934 A1 6/2009 Raschdorf, Jr. et al.
2009/0177288 A1 7/2009 Wallsten
2009/0198227 A1 8/2009 Prakash
2009/0204128 A1 8/2009 Lamson et al.
2010/0010631 A1 1/2010 Otte et al.
2010/0023022 A1 1/2010 Zeiner et al.
2010/0023024 A1 1/2010 Zeiner et al.
2010/0023025 A1 1/2010 Zeiner et al.
2010/0023026 A1 1/2010 Zeiner et al.
2010/0030262 A1 2/2010 McLean et al.
2010/0030263 A1 2/2010 Cheng et al.
2010/0049188 A1 2/2010 Nelson et al.
2010/0063351 A1 3/2010 Witzmann et al.
2010/0063542 A1 3/2010 Burg et al.
2010/0114162 A1 5/2010 Bojarski et al.
2010/0130815 A1 5/2010 Gross et al.
2010/0191045 A1 7/2010 Gobron et al.
2010/0256442 A1 10/2010 Ogdahl et al.
2010/0261950 A1 10/2010 Lund et al.
2010/0286106 A1 11/2010 Gat et al.
2010/0286679 A1 11/2010 Hoey et al.
2010/0286717 A1 11/2010 Heinrich et al.
2010/0298948 A1 11/2010 Hoey et al.
2010/0324669 A1 12/2010 Hlavka et al.
2011/0040312 A1 2/2011 Lamson et al.
2011/0046648 A1 2/2011 Johnston et al.
2011/0060349 A1 3/2011 Cheng et al.
2011/0077676 A1 3/2011 Sivan et al.
2011/0082471 A1 4/2011 Holcomb et al.
2011/0105841 A1 5/2011 Kutikov et al.
2011/0144423 A1 6/2011 Tong et al.
2011/0152839 A1 6/2011 Cima et al.
2011/0160747 A1 6/2011 McLean et al.
2011/0166564 A1 7/2011 Merrick et al.
2011/0172755 A1 7/2011 Nelson et al.
2011/0190758 A1 8/2011 Lamson et al.
2011/0196393 A1 8/2011 Eliachar et al.
2011/0202052 A1 8/2011 Gelbart et al.
2011/0218387 A1 9/2011 Lamson et al.
2011/0245828 A1 10/2011 Baxter et al.
2011/0276081 A1 11/2011 Kilemnik
2011/0276086 A1 11/2011 Al-Qbandi et al.
2012/0010645 A1 1/2012 Feld
2012/0041533 A1 2/2012 Bertolino et al.
2012/0041534 A1 2/2012 Clerc et al.
2012/0059387 A1 3/2012 Schanz et al.
2012/0165837 A1 6/2012 Belman et al.
2012/0203250 A1 8/2012 Weir et al.
2012/0245600 A1 9/2012 McLean et al.
2012/0265006 A1 10/2012 Makower et al.
2013/0096582 A1 4/2013 Cheng et al.
2013/0178871 A1 7/2013 Koogle et al.
2013/0197547 A1 8/2013 Fukuoka et al.
2013/0211431 A1 8/2013 Wei et al.
2013/0253574 A1 9/2013 Catanese et al.
2013/0253662 A1 9/2013 Lamson et al.
2013/0261383 A1 10/2013 Catanese et al.

(56) References Cited

U.S. PATENT DOCUMENTS

2013/0261665 A1 10/2013 Yeung et al.
2013/0267772 A1 10/2013 Catanese et al.
2013/0268001 A1 10/2013 Catanese et al.
2013/0274799 A1 10/2013 Catanese et al.
2013/0289342 A1 10/2013 Tong et al.
2013/0296639 A1 11/2013 Lamson et al.
2013/0296889 A1 11/2013 Tong et al.
2013/0296935 A1 11/2013 McLean et al.
2013/0325143 A1 12/2013 Lamson et al.
2014/0005473 A1 1/2014 Catanese et al.
2014/0005690 A1 1/2014 Catanese et al.
2014/0012192 A1 1/2014 Bar-On et al.
2014/0031835 A1 1/2014 Viker et al.
2014/0088587 A1 3/2014 Merrick et al.
2014/0180067 A1 6/2014 Stigall et al.
2014/0207179 A1 7/2014 Farhangnia et al.
2014/0221981 A1 8/2014 Cima et al.
2014/0236230 A1 8/2014 Johnston et al.
2014/0275756 A1 9/2014 Bender et al.
2014/0288637 A1 9/2014 Clerc et al.
2014/0296881 A1 10/2014 Ranucci et al.
2015/0025652 A1 1/2015 McLean et al.
2015/0112299 A1 4/2015 Forbes et al.
2015/0127050 A1 5/2015 Lamson et al.
2015/0157309 A1 6/2015 Bird
2015/0257908 A1 9/2015 Chao et al.
2015/0335393 A1 11/2015 Ciulla et al.
2015/0351743 A1 12/2015 Stiggelbout
2016/0000455 A1 1/2016 Golan et al.
2016/0022265 A1 1/2016 Kawaura et al.
2016/0038087 A1 2/2016 Hunter
2016/0045297 A1 2/2016 Siegel et al.
2016/0051735 A1 2/2016 Slepian
2016/0081736 A1 3/2016 Hoey et al.
2016/0089140 A1 3/2016 Kawaura et al.
2016/0095685 A1 4/2016 Vemuri et al.
2016/0096009 A1 4/2016 Feld
2016/0120647 A1 5/2016 Rogers et al.
2016/0206370 A1 7/2016 Fruland et al.
2016/0242894 A1 8/2016 Davis
2016/0302904 A1 10/2016 Ogdahl et al.
2016/0317180 A1 11/2016 Kilemnik
2017/0000598 A1 1/2017 Bachar
2017/0128741 A1 5/2017 Keltner et al.
2017/0135830 A1 5/2017 Harkin et al.
2017/0156723 A1 6/2017 Keating et al.
2018/0103945 A1 4/2018 Ciulla et al.
2018/0146964 A1 5/2018 Garcia et al.
2018/0318114 A1 11/2018 Huang et al.
2018/0353181 A1 12/2018 Wei
2019/0125334 A1 5/2019 Tong et al.
2019/0125516 A1 5/2019 Lamson et al.
2019/0365522 A1 12/2019 Lamson et al.
2020/0022692 A1 1/2020 Lamson et al.
2020/0038213 A1 2/2020 Bly et al.
2020/0121442 A1 4/2020 Askeland
2020/0187931 A1 6/2020 Lamson et al.
2021/0145619 A1 5/2021 Bly et al.
2021/0161641 A1 6/2021 Bachar
2021/0161642 A1 6/2021 Jen et al.
2021/0307641 A1 10/2021 Rumbles et al.
2021/0378659 A1 12/2021 Lamson et al.
2021/0378784 A1 12/2021 Welch et al.
2022/0000445 A1 1/2022 Datta et al.
2022/0031357 A1 2/2022 Cutts et al.
2022/0031358 A1 2/2022 Yarra et al.
2022/0031389 A1 2/2022 Fischell et al.
2022/0061834 A1 3/2022 Chung et al.
2022/0125499 A1 4/2022 Hoey et al.
2022/0133462 A1 5/2022 Kilemnik
2022/0142464 A1 5/2022 Petroff et al.
2022/0240921 A1 8/2022 Catanese et al.
2022/0240925 A1 8/2022 Epstein et al.
2022/0249219 A1 8/2022 Chung et al.
2022/0265262 A1 8/2022 Melsheimer
2022/0273918 A1 9/2022 Ghriallais et al.
2022/0378577 A1 12/2022 Anderson et al.
2022/0395363 A1 12/2022 Ghriallais et al.
2023/0022482 A1 1/2023 Dhavale
2023/0200802 A1 6/2023 Catanese, III
2023/0225720 A1 7/2023 Lamson et al.
2023/0225851 A1 7/2023 Lamson et al.
2023/0293166 A1 9/2023 Lamson et al.

FOREIGN PATENT DOCUMENTS

CN 101795641 A 8/2010
CN 102112064 B 6/2014
CN 105852938 A 8/2016
CN 105919695 A 9/2016
CN 109675177 A 4/2019
CN 211156119 U 8/2020
CN 112891032 A 6/2021
CN 216221843 U 4/2022
DE 10159470 A1 6/2003
DE 102019101987 A1 7/2020
EP 0246836 B1 12/1991
EP 0464480 A1 1/1992
EP 0274846 B1 2/1994
EP 0632999 A1 1/1995
EP 0667126 A1 8/1995
EP 1016377 A2 7/2000
EP 1482841 A1 12/2004
EP 1082941 B1 3/2005
EP 1006909 B1 1/2007
EP 1852071 A2 11/2007
EP 1584295 B1 2/2008
EP 1884198 A2 2/2008
EP 1884199 A1 2/2008
EP 1670361 B1 4/2008
EP 1331886 B1 12/2008
EP 1482840 B1 12/2008
EP 2243507 A1 10/2010
EP 1484023 B1 5/2011
EP 2345373 A1 7/2011
EP 2345374 A1 7/2011
EP 2049023 B1 12/2014
EP 3167845 A1 5/2017
FR 2750031 A1 12/1997
JP 5836559 A 3/1983
JP 09122134 5/1997
JP 3370300 B2 1/2003
JP 2004344427 A 12/2004
JP 2009521278 A 6/2009
JP 2011529745 A 12/2011
JP 2012143622 A 8/2012
JP 2023502729 A 1/2023
KR 20060009698 A 2/2006
KR 101534820 B1 7/2015
RU 2062121 C1 6/1996
RU 2112571 C1 6/1998
RU 2128012 C1 3/1999
RU 2221501 C2 1/2004
SU 825094 A1 4/1981
WO 1987001270 A1 3/1987
WO 1992010142 A1 6/1992
WO 1993004727 A1 3/1993
WO 1993015664 A1 8/1993
WO 1994026170 A1 11/1994
WO 1995000818 A1 1/1995
WO 2000040159 A1 7/2000
WO 2001026588 A2 4/2001
WO 2001028432 A1 4/2001
WO 2001039671 A1 6/2001
WO 2001049195 A1 7/2001
WO 2001095818 A1 12/2001
WO 2002028289 A1 4/2002
WO 2002030335 A2 4/2002
WO 2002032321 A1 4/2002
WO 2002058577 A1 8/2002
WO 2003039334 A2 5/2003
WO 2003077772 A1 9/2003
WO 2004000159 A2 12/2003
WO 2004017845 A1 3/2004

(56) References Cited

FOREIGN PATENT DOCUMENTS

| | | | |
|---|---|---|---|
| WO | 2004019787 | A2 | 3/2004 |
| WO | 2004019788 | A2 | 3/2004 |
| WO | 2004030569 | A2 | 4/2004 |
| WO | 2004066875 | A1 | 8/2004 |
| WO | 2004080529 | A2 | 9/2004 |
| WO | 2004103189 | A1 | 12/2004 |
| WO | 2005034738 | A2 | 4/2005 |
| WO | 2005065412 | A2 | 7/2005 |
| WO | 2005094447 | A2 | 10/2005 |
| WO | 2006127241 | A2 | 11/2006 |
| WO | 2006127431 | A2 | 11/2006 |
| WO | 2007048437 | A1 | 5/2007 |
| WO | 2007053516 | A2 | 5/2007 |
| WO | 2007064906 | A2 | 6/2007 |
| WO | 2007075981 | A2 | 7/2007 |
| WO | 2008002340 | A2 | 1/2008 |
| WO | 2008006084 | A2 | 1/2008 |
| WO | 2008014191 | A2 | 1/2008 |
| WO | 2008043044 | A2 | 4/2008 |
| WO | 2008043917 | A2 | 4/2008 |
| WO | 2008097942 | A1 | 8/2008 |
| WO | 2008132735 | A1 | 11/2008 |
| WO | 2008142677 | A2 | 11/2008 |
| WO | 2009009617 | A1 | 1/2009 |
| WO | 2009072131 | A2 | 6/2009 |
| WO | 2010011832 | A1 | 1/2010 |
| WO | 2010014821 | A2 | 2/2010 |
| WO | 2010014825 | A1 | 2/2010 |
| WO | 2010065214 | A2 | 6/2010 |
| WO | 2010086849 | A1 | 8/2010 |
| WO | 2010106543 | A2 | 9/2010 |
| WO | 2011084712 | A1 | 7/2011 |
| WO | 2012018446 | A2 | 2/2012 |
| WO | 2012028843 | A1 | 3/2012 |
| WO | 2012079548 | A1 | 6/2012 |
| WO | 2012079549 | A2 | 6/2012 |
| WO | 2012091952 | A2 | 7/2012 |
| WO | 2012091954 | A2 | 7/2012 |
| WO | 2012091955 | A2 | 7/2012 |
| WO | 2012091956 | A2 | 7/2012 |
| WO | 2012123950 | A2 | 9/2012 |
| WO | 2014003987 | A1 | 1/2014 |
| WO | 2014035506 | A2 | 3/2014 |
| WO | 2014145381 | A1 | 9/2014 |
| WO | 2014153219 | A1 | 9/2014 |
| WO | 2014200764 | A1 | 12/2014 |
| WO | 2015101975 | A1 | 7/2015 |
| WO | 2016134166 | A1 | 8/2016 |
| WO | 2017017499 | A1 | 2/2017 |
| WO | 2017081326 | A2 | 5/2017 |
| WO | 2017112856 | A1 | 6/2017 |
| WO | 2021190092 | A1 | 9/2021 |

OTHER PUBLICATIONS

Berges, Richard, et al. "Alternative Minimalinvasive Therapien Beim Benignen Prostatasyndrom", Medizin, Jg. 104, Heft 37, Sep. 14, 2007.

Borzhievski, et al., "Tactics of the Surgical Treatment of Patients With Prostatic Adenoma and Acute Urinary Retention," Urologia Nefrol (Mosk), Jan.-Feb. 1987, (1):39-43.

European Search Report for EP Application No. 06770621.8, dated Sep. 20, 2012.

European Search Report for EP Application No. 06845991.6, dated Mar. 22, 2013.

European Search Report for EP Application No. 07840462.1, dated May 29, 2012.

European Search Report for EP Application No. 08729001.1, dated Feb. 4, 2014.

European Search Report for EP Application No. 08772483.7, dated Feb. 12, 2015.

European Search Report for EP Application No. 11154962.2, dated May 19, 2011.

European Search Report for EP Application No. 11154976.2, dated Jun. 6, 2011.

European Search Report for EP Application No. 11814950.9, dated Sep. 8, 2015.

European Search Report for EP Application No. 11852778.7, dated Nov. 19, 2015.

European Search Report for EP Application No. 11854148.1, dated Oct. 20, 2017.

European Search Report for EP Application No. 13810314.8, dated Apr. 6, 2016.

European Search Report for EP Application No. 17150545.6, dated Sep. 11, 2017.

Hartung, Rudolf, et al. "Instrumentelle Therapie der benignen Prostatahyperplasie", Medizin, Deutsches Arzteblatt 97, Heft 15, Apr. 14, 2000.

Hofner, Klaus, et al., "Operative Therapie des benignen Prostatasyndroms", Medizin, Dtsch Arztebl, 2007; 104(36): A2424-9.

Hubmann, R. "Geschichte der transurethralen Prostataeingriffe", Geschichte der Medizin, Urologe [B], 2000, 40:152-160.

International Search Report for PCT Application No. PCT/US2006/019372, dated May 2, 2008.

International Search Report for PCT Application No. PCT/US2006/048962, dated Dec. 10, 2008.

International Search Report for PCT Application No. PCT/US2007/074019, dated Jul. 25, 2008.

International Search Report for PCT Application No. PCT/US2008/053001, dated Jun. 17, 2008.

International Search Report for PCT Application No. PCT/US2008/069560, dated Sep. 8, 2008.

International Search Report for PCT Application No. PCT/US2009/052271, dated Apr. 7, 2010.

International Search Report for PCT Application No. PCT/US2009/052275, dated Oct. 9, 2009.

International Search Report for PCT Application No. PCT/US2011/041200, dated Feb. 17, 2012.

International Search Report for PCT Application No. PCT/US2011/065348, dated Jun. 21, 2012.

International Search Report for PCT Application No. PCT/US2011/065358, dated Jun. 21, 2012.

International Search Report for PCT Application No. PCT/US2011/065377, dated Aug. 29, 2012.

International Search Report for PCT Application No. PCT/US2011/065386, dated Jun. 28, 2012.

International Search Report for PCT Application No. PCT/US2013/044035, dated Sep. 6, 2013.

Jonas, U., et al., "Benigne Prostatahyperplasie", Der Urologe 2006—[Sonderheft] 45:134-144.

Kruck, S., et al., "Aktuelle Therapiemoglichkeiten des Benignen Prostata-Syndroms", J Urol Urogynakol, 2009; 16(1):19-22.

Miyake, Osamu. "Medical Examination and Treatment for BPH," Pharma Med, vol. 22, No. 3, 2004, p. 97-103.

Reich, O., et al., "Benignes Prostatasyndrom (BPS)," Der Urologe A Issue vol. 45, No. 6, Jun. 2006, p. 769-782.

Schauer, P., et al. "New applications for endoscopy: the emerging field of endoluminal and transgastric bariatric surgery", Surgical Endoscopy, (Apr. 24, 2006), 10 pgs.

Sharp, Howard T., M.D., et al. "Instruments and Methods—The 4-S Modification of the Roeder Knot: How to Tie It", Obstetrics & Gynecology, p. 1004-1006, vol. 90, No. 6, Dec. 1997.

Takashi, Daito. "Low-Invasive Treatment for BPH", Medico vol. 34, No. 10, p. 366-369, 2000.

Teruhisa, Ohashi. "Urinary Dysfunction by Lower Urinary Tract Obstraction in Male", Pharma Medica, vol. 8, No. 8, p. 35-39, 1990.

Tomohiko, Koyanagi, et al., "Surgery View of 21st Century," Urological Surgery, vol. 84, No. 1, p. 47-53, 2001.

Trapeznikov, et al., "New Technologies in the Treatment of Benign Prostatic Hyperplasia", Urologia Nefrol (Mosk), Jul.-Aug. 1996, (4):41-47.

U.S. Appl. No. 16/433,054, Non-Final Office Action dated Sep. 23, 2019, 6 pgs.

U.S. Appl. No. 16/433,054, Response filed Dec. 18, 2019 to Non-Final Office Action dated Sep. 23, 2019, 16 pgs.

(56) References Cited

OTHER PUBLICATIONS

Yeung, Jeff. "Treating Urinary Stress Incontenance Without Incision with Endoscopic Suture Anchor & Approximating Device," Aleeva Medical, Inc., 2007.
European Extended Search Report and Search Opinion dated Jun. 16, 2023, in EP Application No. 23169061.1.
Office Action dated Jun. 22, 2023, in co-pending U.S. Appl. No. 18/181,914.
Response to Office Action filed Sep. 21, 2023, in co-pending U.S. Appl. No. 18/181,914.
U.S. Appl. No. 16/234,282, filed Dec. 26, 2018.

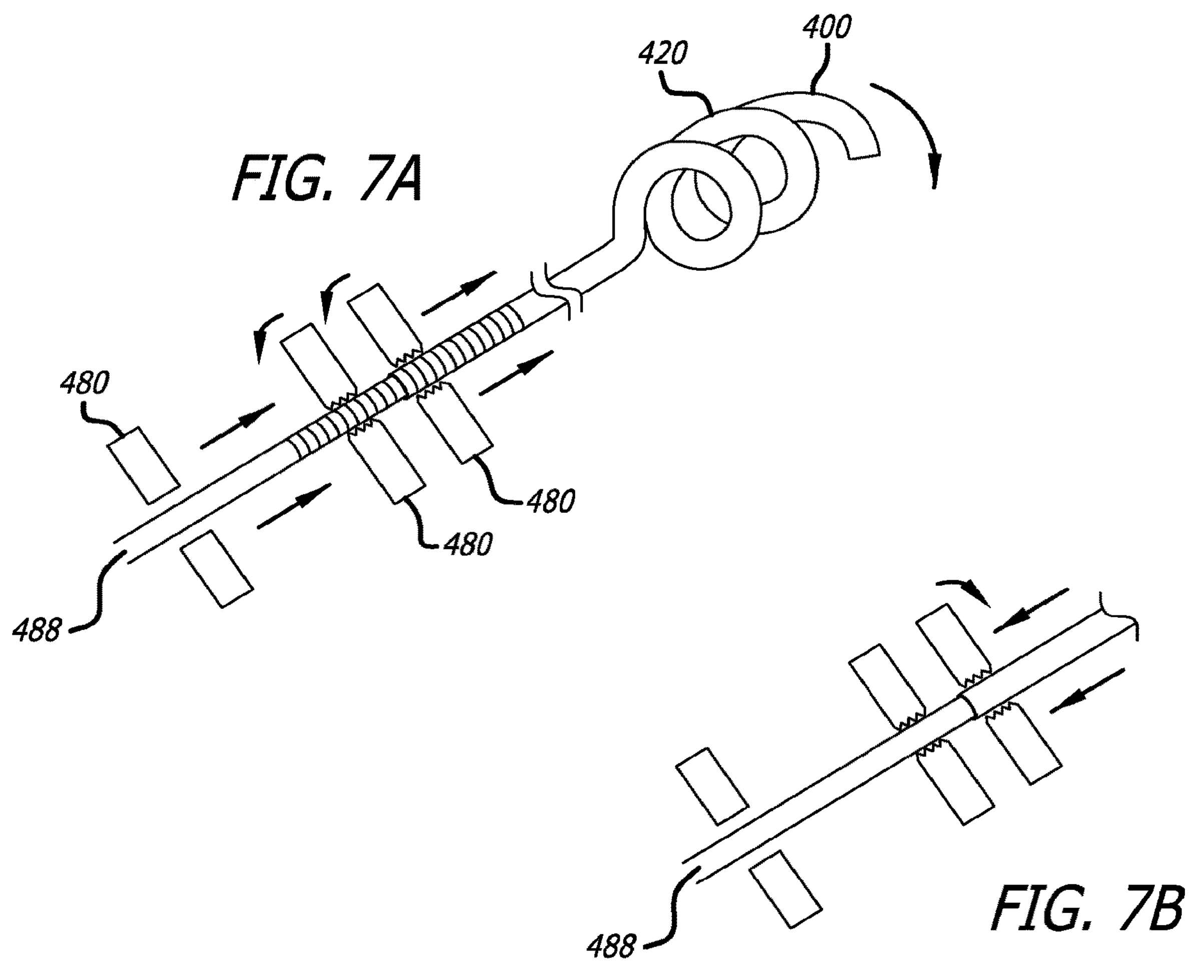
FIG. 7A
400
420
480
480
480
488
488
FIG. 7B
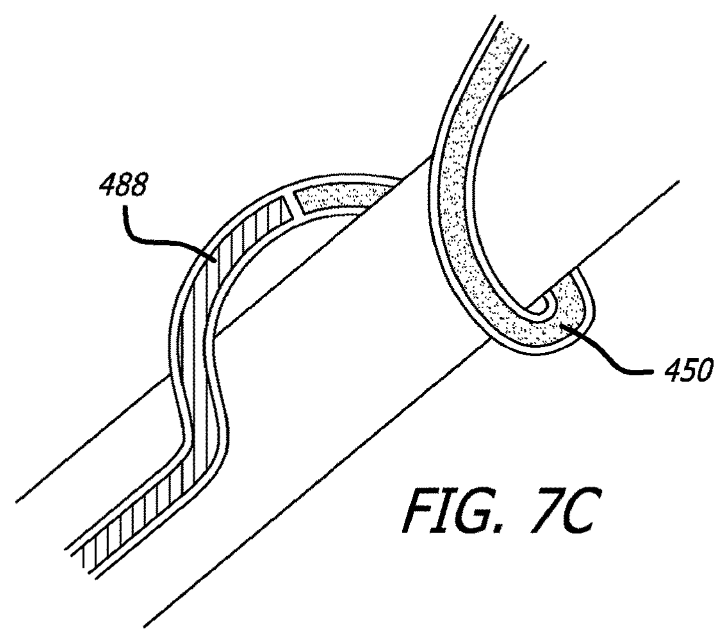
488
450
FIG. 7C

1310

2
1300

1400

1520
1500
1510

2

DEVICES, SYSTEMS AND METHODS FOR TREATING BENIGN PROSTATIC HYPERPLASIA AND OTHER CONDITIONS

CROSS-REFERENCE TO RELATED APPLICATIONS

This application is a continuation of U.S. application Ser. No. 16/234,282, filed Dec. 27, 2018, now abandoned, which is a continuation of U.S. application Ser. No. 13/830,811, filed Mar. 14, 2013, now U.S. Pat. No. 10,195,014, both entitled "Devices, Systems and Methods for Treating Benign Prostatic Hyperplasia and Other Conditions," and each of which is expressly incorporated herein by reference.

BACKGROUND

The present invention relates generally to medical devices and methods and more particularly to devices, systems and methods for treating conditions wherein a tissue (e.g., the prostate gland) has a) become enlarged and/or b) undergone a change in form, position, structure, rigidity or force exertion with respect to another anatomical structure and/or c) has begun to impinge upon or compress an adjacent anatomical structure (e.g., the urethra).

Benign Prostatic Hyperplasia (BPH) is one of the most common medical conditions that affect men, especially elderly men. It has been reported that, in the United States more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

Despite extensive efforts in both the medical device and pharmaco-therapeutic fields, current treatments remain only partially effective and are burdened with significant side effects. Certain devices used to displace urethral tissue, such as urethral stents, can become encrusted due to exposure to urine. This encrustation is an undesirable and problematic side effect.

Thus, there remains a need for the development of new devices, systems and methods for treating BPH as well as other conditions in which one tissue or anatomical structure impinges upon or compresses another tissue or anatomical structure.

SUMMARY

Certain embodiments related to a system for enlarging a lumen of a prostatic urethra. The system includes a delivery tool and an implant carried by the delivery tool. The implant is shaped to at least partially circumscribe the prostatic urethra of a patient. The system also includes a depth guide. The depth guide and delivery tool cooperate to deploy the implant within the peri-urethral space and thereby enlarge the lumen of the prostatic urethra.

In some embodiments, the delivery tool has a sharp surface configured to penetrate the urethral wall. In some embodiments, delivery tool delivers energy to prostatic tissue. In some embodiments, the implant has a sharp surface configured to penetrate the urethral wall. In some embodiments, the implant is carried externally to at least part of the delivery tool. In some embodiments, the implant is carried internally to at least part of the delivery tool. In some embodiments, the system includes a pusher coupled to the implant. In some embodiments, the system includes a locking mechanism coupled to at least one of the delivery tool, the implant, or the pusher. In some embodiments, the implant includes a first section and a second section, and the first section is comparatively more flexible than the second section. In some embodiments, the implant is self expanding. In some embodiments, the delivery tool and the implant each have a radius of curvature and the delivery tool radius of curvature is greater than the implant radius of curvature. In some embodiments, the implant includes a first section and a second section, and the first section is frictionally-engaged with the second section. In some embodiments, the implant is configured to be deployed by overcoming the frictional engagement.

BRIEF DESCRIPTION OF THE DRAWINGS

FIGS. 7A through 7C illustrate views of a method for placing an implant that is contained within a delivery tool according to an embodiment. A pusher and locking mechanisms facilitate delivery of the implant.

DETAILED DESCRIPTION

Figure 1A:
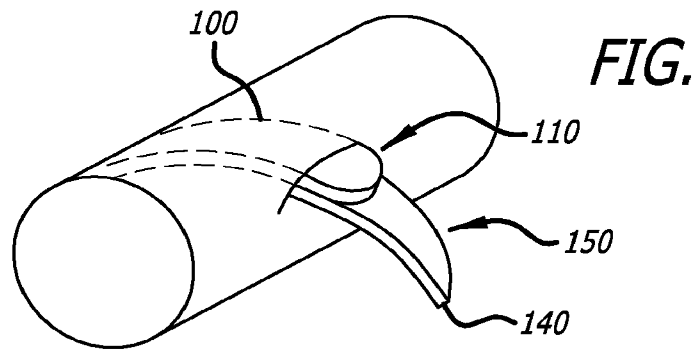
FIGS. 1A and 1B illustrate views of an embodiment in which a depth guide facilitates the delivery of an implant.

The following description of the preferred embodiments of the invention is not intended to limit the invention to these preferred embodiments, but rather to enable any person skilled in the art to make and use this invention. Disclosed herein are systems and methods for treating conditions wherein a tissue (e.g., the prostate gland) has a) become enlarged and/or b) undergone a change in form, position, structure, rigidity or force exertion with respect to another anatomical structure and/or c) has begun to impinge upon or compress an adjacent anatomical structure (e.g., the urethra).

Mechanically displacing prostatic tissue so as to enlarge the lumen of the prostatic urethra is an attractive long-term solution to BPH. However, as described above, chronic exposure of an implant to urine is undesirable. According to embodiments described herein, implants placed near the urethral boundary of the prostate can provide the mechanical forces necessary to enlarge the lumen of the prostatic urethra while avoiding chronic exposure to urine.

For the purposes of this application, the area of the prostate gland near the urethral surface can be referred to as the extra-urethral portion of the prostate. The extra-urethral portion of the prostate is also that portion of the prostate near enough to the urethral boundary such that the prostatic tissue is comparatively less spongy than the central part of the gland. The extra-urethral portion has sufficient mechanical integrity to hold an implant substantially in place. Because the size, shape, and tissue properties of the prostate can vary significantly from one subject to another, this application defines the extra-urethral region in terms of an approximate position relative to the prostatic urethra and in terms of the mechanical properties of the region. The extra-urethral region may also include, or be referred to as, the urethral wall without being limited exclusively to the membrane layer of the prostate immediately adjacent the prostatic urethra. The extra-urethral region may also include, or be referred to as, the peri-urethral region or peri-urethral tissue. Of course, in this application peri-urethral tissue still refers to the region of the urethra within the prostate.

Certain embodiments described herein place implants in the prostate by puncturing, cutting, dissecting, or otherwise penetrating the extra-urethral region of the prostate. In doing so, it is important to avoid puncturing the anatomy in undesirable locations, such as the urethral sphincter, the bladder, and ejaculation ducts. In certain embodiments, more than one extra-urethral implant is desirable to avoid puncturing such locations in the anatomy. For example, multiple implants could be placed such that one implant is distal to the ejaculation ducts and another implant is proximal to the ejaculation ducts. In this way, multiple implants can be used to provide the necessary mechanical dilation of and long-term stability in the urethral lumen while not substantially damaging sensitive parts of the local anatomy.

In certain embodiments, extra-urethral implants include cutting surfaces to facilitate delivery of the implant into tissue. Other surfaces of any delivery device used may be comparatively blunt such that the cutting is focused at a certain surface of the implant.

In certain embodiments, a delivery tool, member, and/or surface is used to cut, penetrate, dissect, separate, or otherwise provide a point of entry and optionally a path through tissue for an implant. In such embodiments, the delivery tool, member, and/or surface can be sharp, pointed, serrated, or otherwise configured to cut tissue. Further, the delivery tool, member, and/or surface can be configured to instead, or in addition, delivery energy (e.g., radio frequency, ultrasound, and/or laser) to tissue to accomplish the penetration.

Figure 1B:
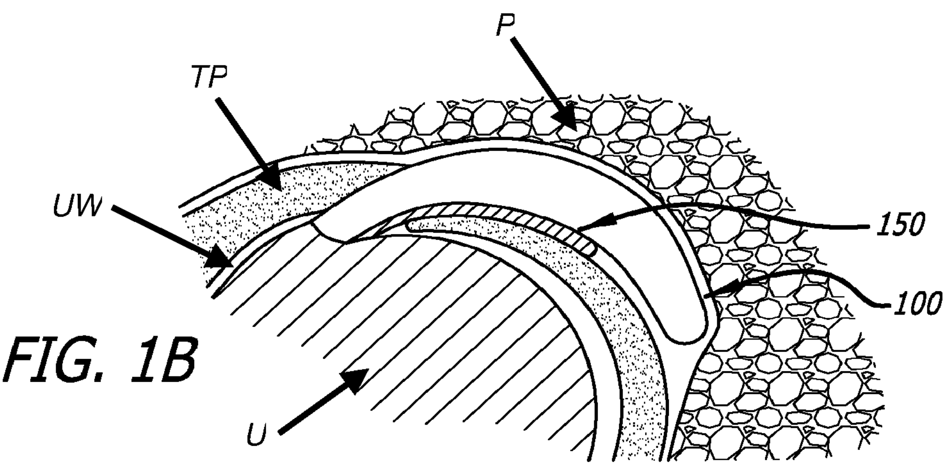

In certain embodiments, it is preferable to use selective blunt dissection in the peri-urethral tissue plane TP. In such embodiments, the blunt edges of a dissection tool or of the implant produce blunt dissection in the peri-urethral tissue plane TP, separating the urethra U from portions of the prostate P. A penetrating tip may be used to exit the urethra U and set the depth of the penetration such that the appropriate tissue plane in the extra-urethral region can be accessed. FIGS. 1A and 1B depict the blunt tip 110 of an extra-urethral implant 100 and the tip 140 of a depth guide 150 deployed to an adjustable depth alongside the blunt tip 110. The depth guide 150 ensures delivery of the extra-urethral implant 100 beyond the urethral wall UW by creating space between the implant and the urethral wall UW. The depth guide 150 can be withdrawn at any point during the implantation of the extra-urethral implant 100. Preferably, the depth guide 150 is kept in place until the extra-urethral implant 100 has been deployed in the extra-urethral region such that the extra-urethral implant 100 mechanically displaces prostatic tissue away from the urethral lumen. The depth guide 150 can be removably fastened to the extra-urethral implant 100 by various methods. For example, the depth guide 150 can be fastened with one way tabs such that the depth guide 150 remains fixed to the extra-urethral implant 100 when the two members are pushed but can be released from in gauge meant with the extra-urethral implant 100 when the depth guide 150 is pulled proximally and the extra-urethral implant 100 is held in place. Other equivalent methods are within the scope of this disclosure.

In certain embodiments, the extra-urethral implant is delivered such that it is "wound up" like a spring prior to delivery. Upon removal of the depth guide 150, the implant 100 is configured to unwind and expand its diameter.

Figure 2:
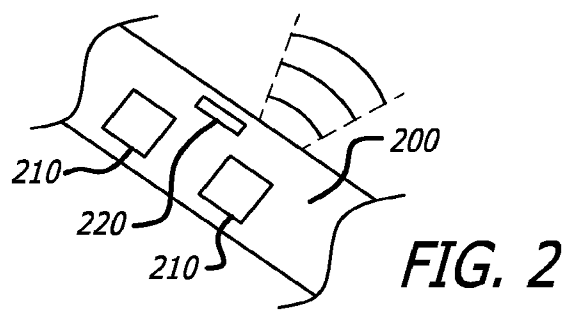
FIG. 2 illustrates views of an embodiment in which transmitters and receivers help determine the position of an implant.
Figure 3:
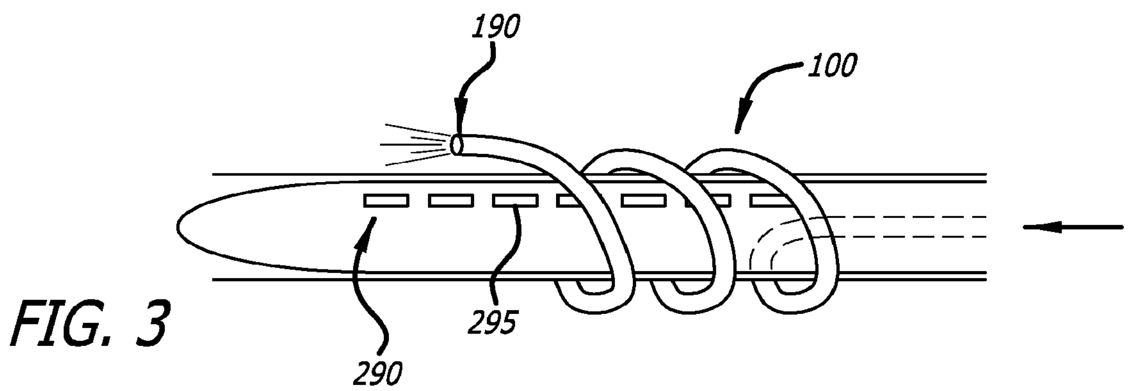
FIG. 3 illustrates the use of an embodiment in which the implant transmits light that helps determine its location within tissue.

In certain embodiments, it is preferable to know the relative locations of the urethral sphincter and bladder with respect to prostate prior to and/or during the implantation of an extra-urethral implant. Further, it may be preferable to know where the extra-urethral implant is being deployed relative to the structures. In such embodiments, the delivery device 200 can include a transurethral imaging device. Typically, imaging devices onboard a delivery device 200 can have transmitters 210 and receivers 210 near the delivery port 220, as depicted in FIG. 2. Other embodiments can provide similar location information using optics systems. For example, in certain embodiments in which the extra-urethral implant is polymeric, the polymeric material can be chosen such that it is capable of transmitting light in addition to having desirable mechanical properties. FIG. 3 depicts the distal end 190 of the implant functions as a beacon, and can be detected by optical sensors 295 on board the delivery device. In one example, the multiple sensors 295 can track the position of the distal end 190 of the implant even though the implant is within the extra-urethral region by detecting the light emitted from the distal end 190 of the implant. By moving the distal end 290 of the delivery device, which allows multiple sensors 295 to collect light, the precise position of the implant can be determined. This kind of precise tracking and positioning can help avoid damaging sensitive parts of the local anatomy.

Figure 4A:
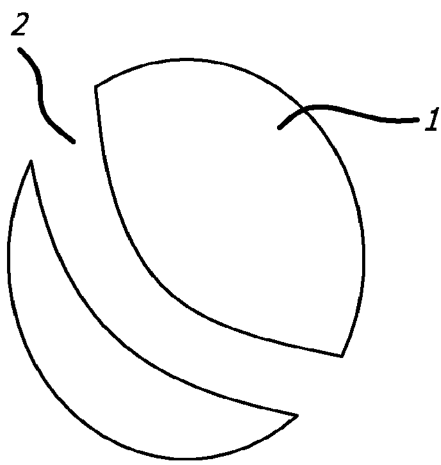
FIGS. 4A through 4E illustrate views of the challenges of implanting a device that straightens a naturally bent urethra.
Figure 4B:
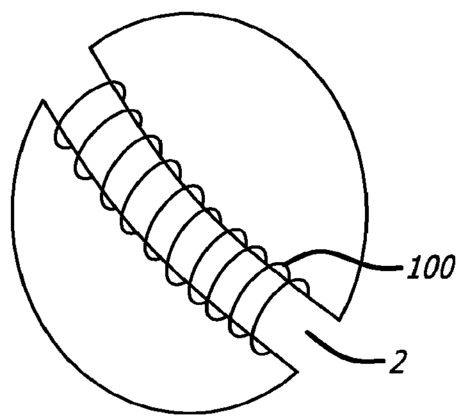
Figure 4C:
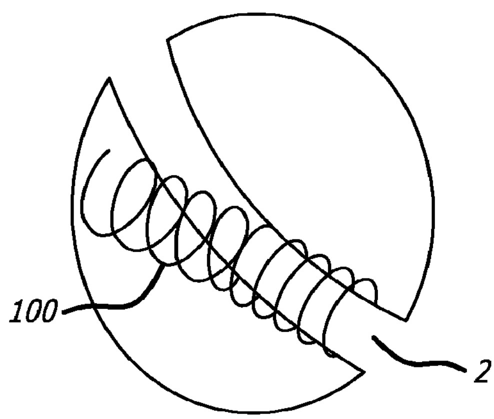
Figure 4D:
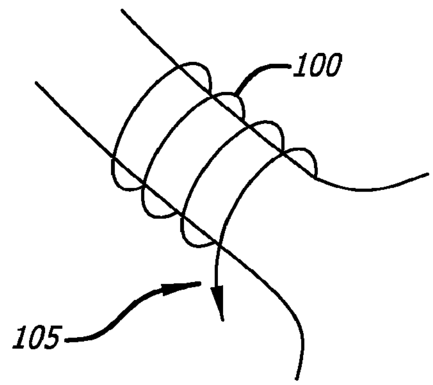
Figure 4E:
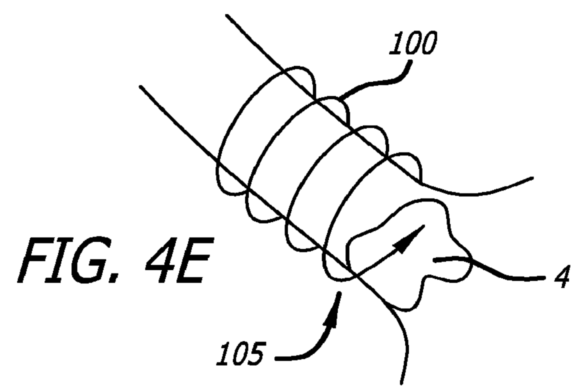

FIGS. 4A through 4E illustrate the challenges of providing a mechanically-resilient implant in the prostatic urethra. FIG. 4A depicts a view of a bend in the urethra 2. Because the implant is driven into and/or through tissue, the implant should have a sufficient degree of stiffness and strength. FIG. 4B depicts implant 100 within the extra-urethral region after having been driven through tissue. FIG. 4B depicts the urethra 2 as now straightened as compared to its previously bent condition depicted in FIG. 4A. However, over time the mechanical resilience, strength, and stiffness of the implant can have unwanted effects, as depicted in FIG. 4C. The implant in FIG. 4C has caused distortions in the prostatic tissue that in turn later caused migration of the implant 100 through tissue. Further, FIGS. 4D and 4E depict the sharp tip 105 of an implant 100 that migrates or cuts through tissue leading to erosion of tissue 4 and exposure of the implant to urine. As discussed above, chronic exposure to urine can lead to encrustation and further complications.

To accommodate this balance between the strength and stiffness needed to penetrate tissue and the flexibility and conformability needed to avoid damaging tissue in a chronic implant environment, it is preferable in certain embodiments to use a two-stage implantation process. In such a two-stage implantation, a stiff, sharp tool is advanced into tissue. Next a softer and/or less stiff implant is left behind when the delivery tool is retracted. In embodiments in which the first stage of implantation is accomplished by delivering energy to tissue, the implant can remain outside the area where energy is being delivered until implantation. In this way, the implant does not experience the delivery energy, which can be advantageous if the delivery energy would have an adverse effect on the implant.

Figure 5:
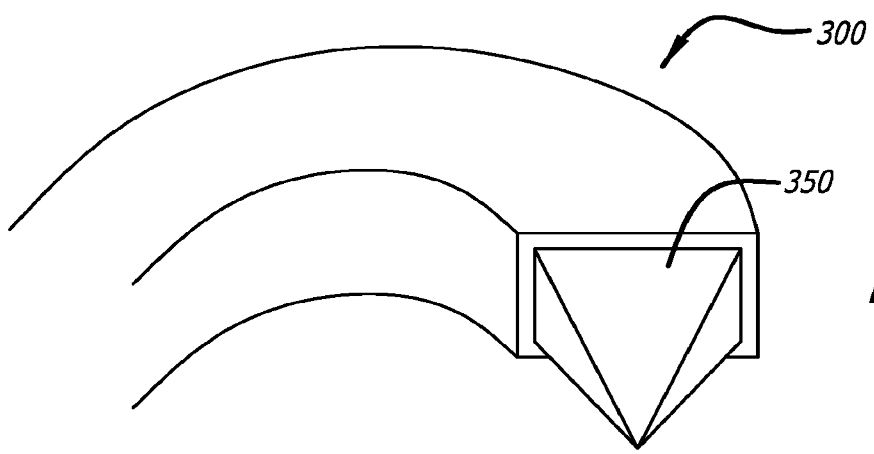
FIG. 5 illustrates a view of a delivery tool and implant in which the implant rides on the outside of the delivery tool according to an embodiment. The delivery tool is stiff and sharp as compared to the implant.

FIG. 5 illustrates a stiff delivery tool 350 and a comparatively less stiff implant 300 to be left behind when the delivery tool 350 is retracted. The core is stiff and sharp, which is preferable for driving into tissue to enable delivery of the more supple sheath implant 300 around the sharp core. Upon retraction, the comparatively less stiff sheath implant 300 is left behind as the extra-urethral implant. Preferably, the sheath has column strength substantial enough such that it does not peel back from the core when the core is being driven through tissue.

Figure 6:
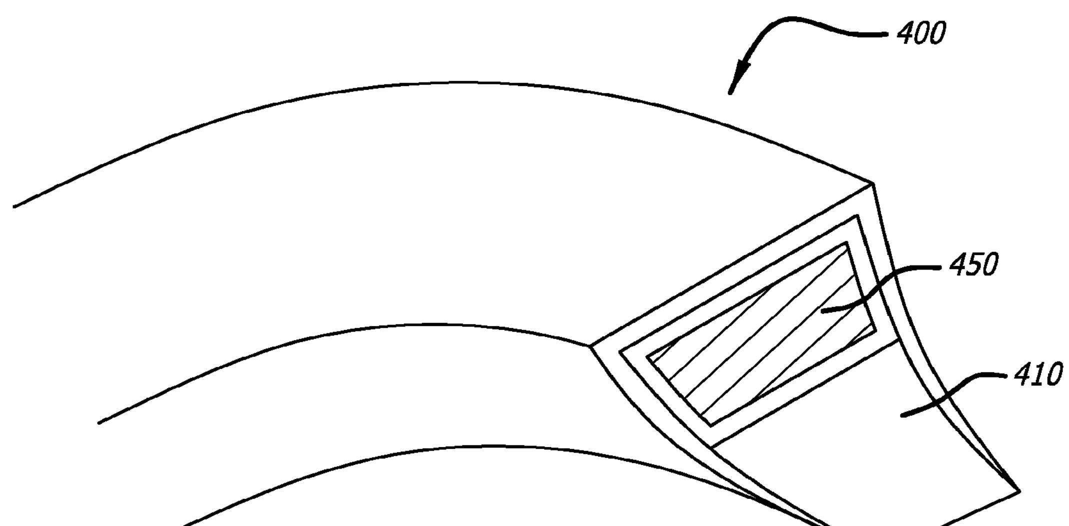
FIG. 6 illustrates a view of a delivery tool and implant in which the implant is contained within the delivery tool according to an embodiment. The delivery tool is stiff and sharp as compared to the implant.

FIG. 6 illustrates another embodiment of a stiff delivery tool 400 and a comparatively less stiff implant 450 to be left behind when to delivery tool 400 is retracted. In this embodiment, the delivery tool 400 is external to the implant 450. The external delivery tool 400 is depicted as having a rectangular cross-section, but other cross-sections that facilitate directed delivery of the extra-urethral implant can also be used. The tip 410 of the delivery tool should be non-coring such that material does not build up at the tip of the delivery tool 400 and retard the progress of the delivery tool 400 and implant 450 through tissue. Advantageously, in this embodiment the implant 450 can have less column strength than the embodiment of FIG. 5 in which the implant is external to the delivery tool because the implant 450 in the embodiment of FIG. 6 is comparatively protected within the delivery tool 400. Further, the implant surface does not pass through tissue during delivery and so the implant 450 sees none of the frictional forces that the implant of the embodiment of FIG. 5 sees since it is external to the delivery tool.

FIGS. 7A through 7C depict the delivery process of embodiments in which both the implant core 450 and the delivery tool 400 are advanced through tissue in the deployment phase. FIG. 7A depicts a helical shape for the distal end 420 of delivery tool 400. Implant core 450 is within this distal end 420 of delivery tool 400. FIG. 7A depicts lock mechanisms 480 at a region proximal to the implant core 450. These lock mechanisms 480 allow the delivery tool 400 and the implant core 450 to be manipulated together or separately by selectively locking or unlocking the delivery tool 400 and the implant core 450 with respect to each other. FIG. 7B depicts delivery school 400 being retracted while the implant pusher 488 is held fixed by some of the locking mechanisms 480. In this way, the internal implant core 450 is extruded into tissue. FIG. 7C further depicts a sectional view to illustrate the implant pusher 488 enabling delivery of the implant 450. The pusher 488 must be long enough to exit the urethra such that the implant 450 is fully embedded away from the urethral lumen, that is, the implant 450 is delivered to an extra-urethral position.

Figure 8A:
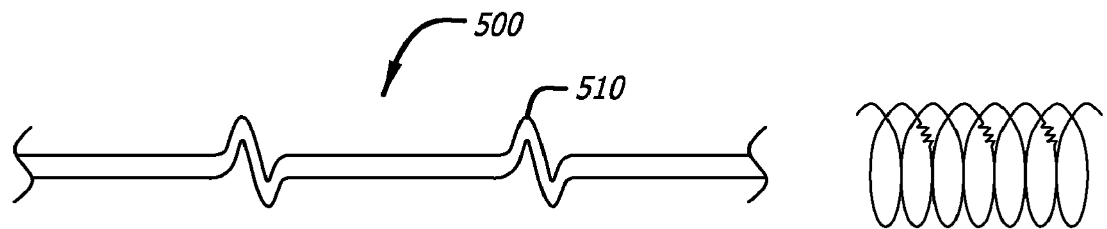
FIGS. 8A through 8C illustrate views of an embodiment of an implant with longitudinal flexibility to accommodate urethral anatomy.
Figure 8B:
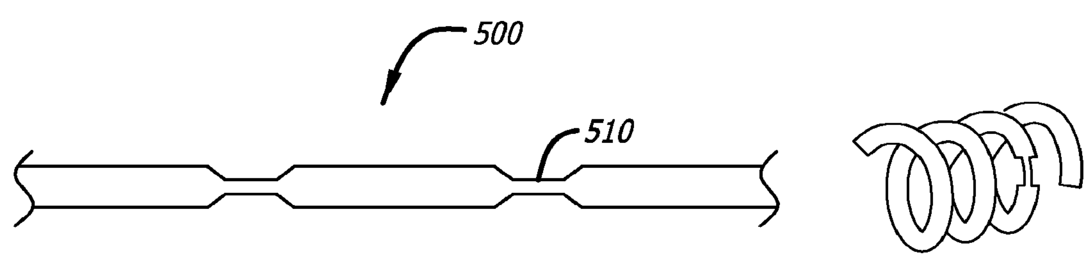
Figure 8C:
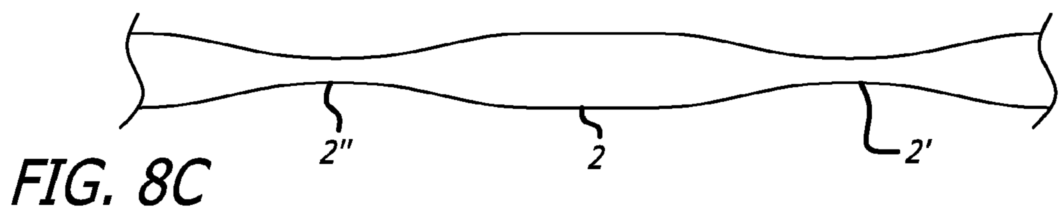

FIGS. 8A through 8C depict embodiments that can accommodate the variations of urethral anatomy while still providing the desired mechanical properties to enlarge the urethral lumen. Extra-urethral implants may need to flex longitudinally to avoid straightening the natural geometry of the urethra. Such straightening could cause discomfort and may lead to migration of the implant within tissue. FIGS. 8A and 8B depict two configurations of an embodiment of a variable strength extra-urethral implant and FIG. 8C depicts the prostatic urethra after implantation of such variable strength extra-urethral implants. As depicted in FIGS. 8A and 8B, an extra-urethral implant can have variable strength segments. Some flexible segments 510 can have hinge-like geometries to relieve longitudinal stress. The extra-urethral implant 500 can act similar to a series of independent rings rather than a straight coil. FIG. 8C depicts wider segments 2' of the urethra 2 in which the stiffer segments of the extra-urethral implant 500 have enlarged the urethral lumen and narrower segments 2" in which the flexible segments 510 have exerted less mechanical before action on the urethra 2. Although the entire length of the prostatic urethra has not been enlarged, it is believed that small narrowed segments coupled with a majority of large segments can still reduce or relieve symptoms of BPH.

Figure 9:
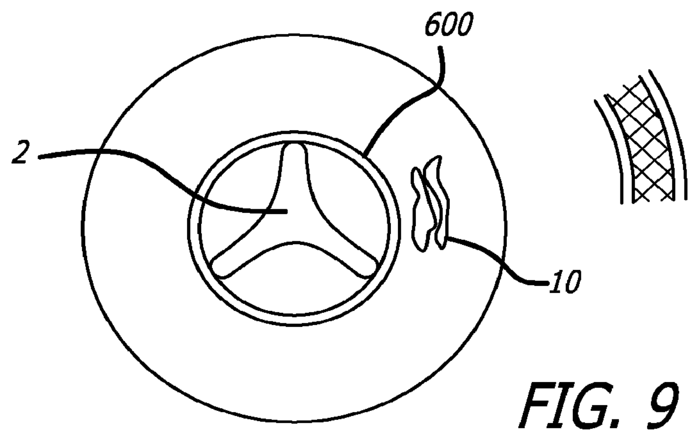
FIG. 9 depicts an embodiment in which the impingement of further hyperplasia on the urethral lumen is limited.

FIG. 9 depicts a benefit of extra-urethral implants 600 that substantially encircle the urethral lumen 2. The benefit of encircling the urethral lumen is that hyperplasia subsequent to implantation of the extra-urethral implant 600 can be physically prevented from impinging on the urethral lumen. The extra-urethral implant 600 provides a physical barrier from further cell growth that narrows the urethral lumen.

Figure 10A:
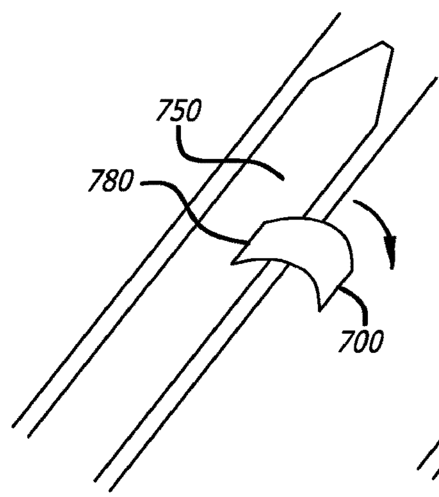
FIGS. 10A through 10C illustrate views of an embodiment in which an implant is placed that provides radial force without significant longitudinal displacement.
Figure 10B:
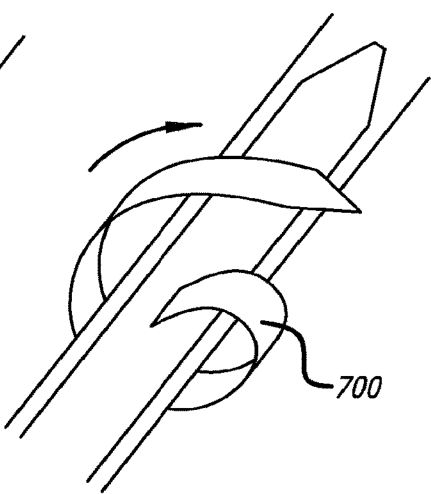
Figure 10C:
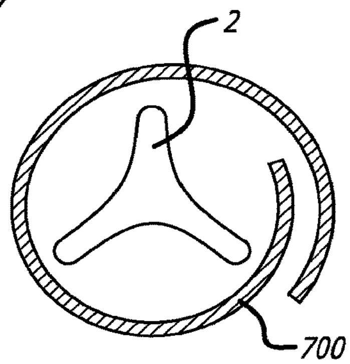

In some embodiments, controlling the extra-urethral implant as it advances longitudinally can be challenging in that it is preferable to keep the implant roughly coaxial with the lumen of the urethra. However, the urethra does not always have a straight geometry. In certain embodiments, the implant can be radially expanding, but without translating significantly along the longitudinal axis of the urethra. FIGS. 10A through 10C depicts an embodiment in which the extra-urethral implant is capable of radial expansion sufficient to displace urethral tissue, but without significant translation along the longitudinal axis of the urethra. FIG. 10A depicts delivery tool 750 within the urethral lumen and extra-urethral implant 700 advancing out of delivery port 780. Extra-urethral implant 700 has a sharp tip which enables it to advance through tissue. Extra-urethral implant 700 is sized and configured such that it provides outwardly radial force to mechanically enlarge the urethral lumen without generating significant longitudinal forces. That is, extra-urethral implant 700 is sized and configured to sufficiently circumscribe, or at least partially circumscribe, the urethral lumen. Multiple extra-urethral implants 700 can be delivered using delivery tool 752 the same prostatic urethra. Delivering multiple extra-urethral implant 700 provides enlargement of the urethral lumen along a length of the prostatic urethra. Such multiple extra-urethral implants 700 also have the benefit of avoiding the straightening problems described above.

Figure 11A:
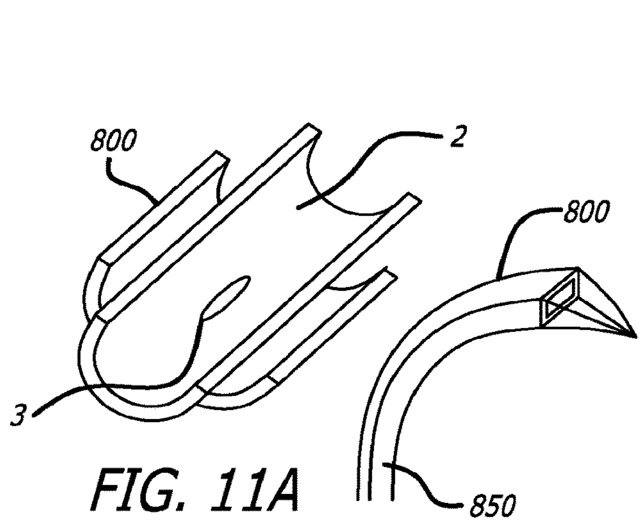
FIGS. 11A through 11C illustrate views of an embodiment in which the implant expands after being placed by a delivery tool. The implant is carried within the delivery tool.
Figure 11B:
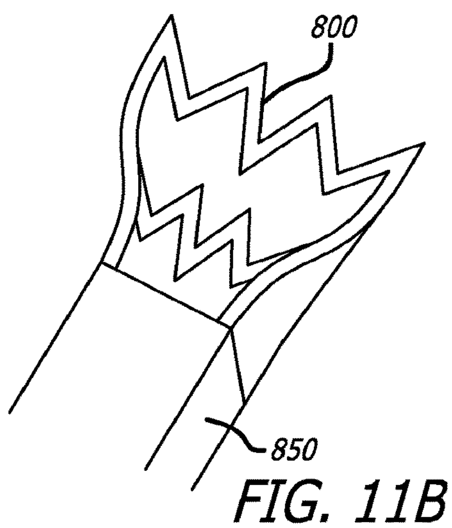
Figure 11C:
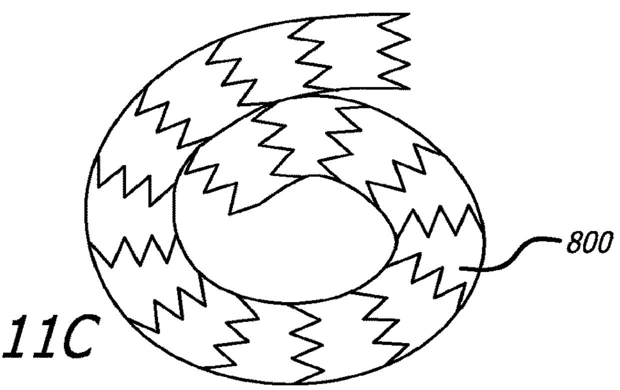

FIGS. 11A through 11C illustrate yet another embodiment of an extra-urethral implant 800. In this embodiment, the deployment of the extra-urethral implant 800 can be in two stages. First, deployment tool 850 cuts a deployment path for the implant. Then, the implant 800 is deployed and, within the peri-urethral region, expands to a larger diameter than the deployment tool 850. FIG. 11A depicts a cross-section of the prostatic urethra 2 with entry hole 3. Extra-urethral implant 800 resides in the peri-urethral space. FIG. 11A also depicts a view of the constrained configuration of implant 800 within deployment tool 850. In FIG. 11B, extra-urethral implant 800 is shown advancing relative to the end of the deployment tool 850 and simultaneously expanding to an expanded configuration. As disclosed in other embodiments herein, extra-urethral implant 800 can be advanced relative to deployment tool 850 by various mechanisms, including but not limited to, a pusher. FIG. 11C depicts extra-urethral implant 800 in an expanded and delivered configuration. In this configuration, extra-urethral implant 800 is shown as having overlapping ends but the implant need only circumscribe enough of the prostatic urethra to create the desired mechanical enlargement of the urethral lumen.

Figure 12A:
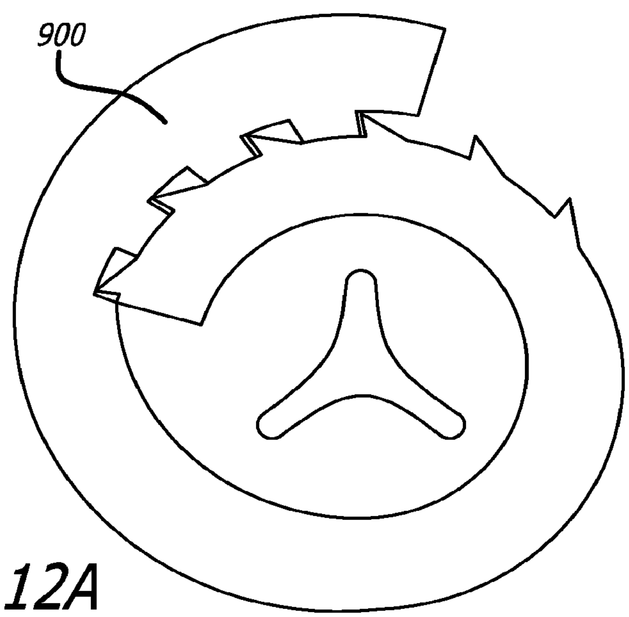
FIGS. 12A through 12B illustrate views of an implant that is frictionally connected to itself and deployed using a dilating member according to an embodiment.
Figure 12B:
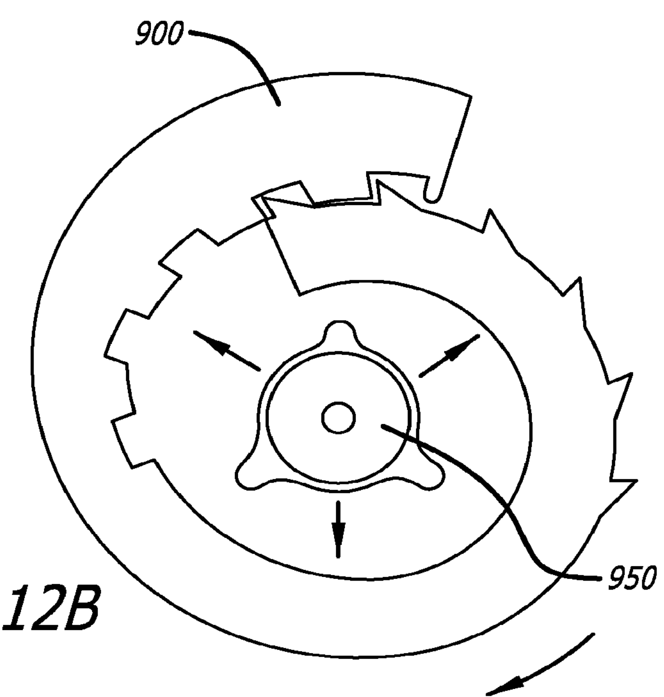

FIGS. 12A and 12B depict another embodiment of an extra-urethral implant 900. In this embodiment, the implant is frictionally connected with itself such that after initial deployment, or at a later stage, the implant could be expanded through dilation of urethra and ratcheting of the frictionally connected surfaces. FIGS. 12A and 12B depict a ring having an at least partially external loop that is in interlocking contact with an at least partially internal loop. A dilation member 950, such as a balloon, within the urethra is used to force peri-urethral tissue outward. These outward forces cause the implant to ratchet to a larger diameter. The implant will then hold peri-urethral tissue further way radially from the lumen of the urethra. This implant can be implanted initially using any of the delivery and deployment methods described herein.

Figure 13:
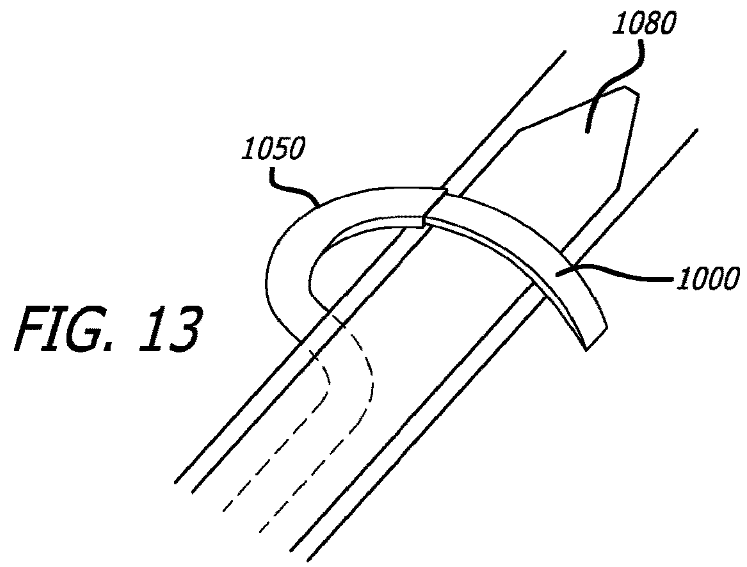
FIG. 13 illustrates views of an embodiment in which the delivery tool has a tighter radius than the implant.

One of the challenges of expanding a narrowed urethral lumen with a coil or ring-like device is that the lumen initially has a smaller diameter and tighter radius of curvature than it will have after treatment. Some of the embodiments described herein address that challenge by expanding after deployment. FIG. 13 illustrates an embodiment in which the radius of cutting tool 1050 is tighter than the radius of extra-urethral implant 1000. Cutting tool 1050 is deployed from delivery tool 1080 and cuts into the peri-urethral space to provided deployment path for extra-urethral implant 1000. Cutting tool 1050 sets the initial deployment trajectory of the extra-urethral implant 1000, but after delivery by advancing with respect to the cutting tool 1050 the extra-urethral implant 1000 can assume greater diameter and corresponding lesser radius of curvature.

Figure 14A:
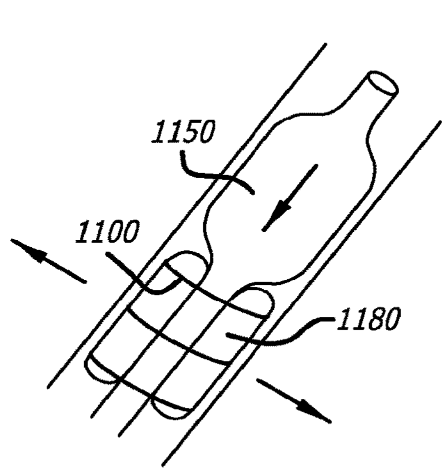
FIGS. 14A through 14C illustrative views of an embodiment in which the urethral lumen is enlarged prior to delivery of the implant.
Figure 14B:
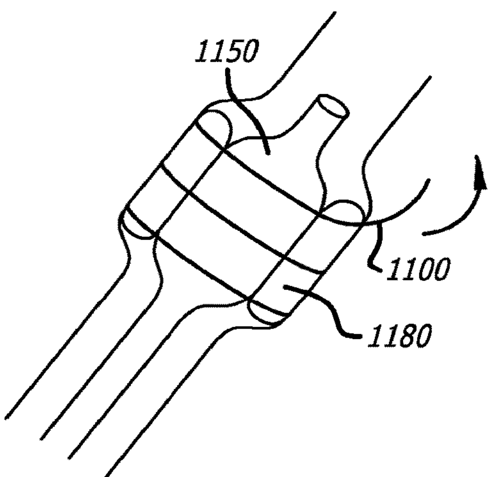
Figure 14C:
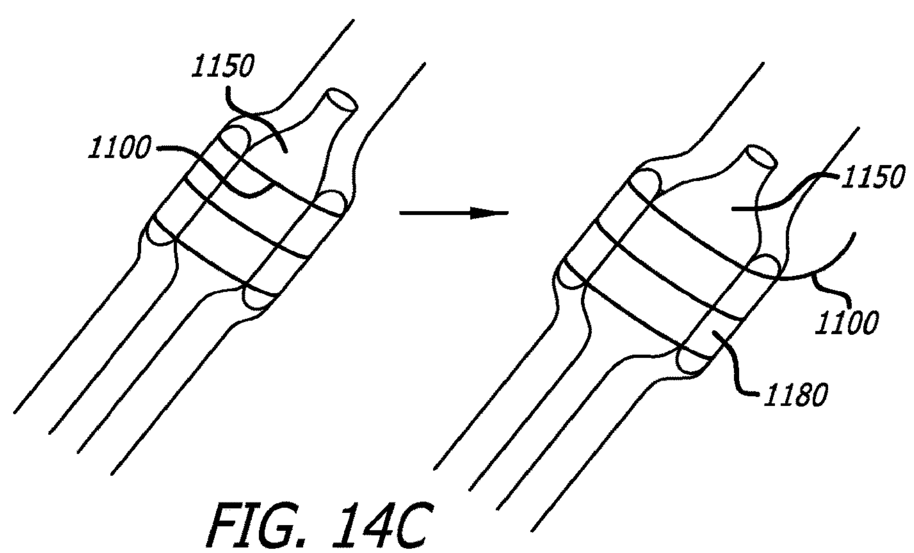

In yet another embodiment depicted in FIGS. 14A through 14C, a delivery system 1150 can be expanded at the delivery site such that the coil diameter starts deployment at the maximal urethral diameter. That is, rather than using the extra-urethral implant 1100 to expand the urethral diameter, the expansion device 1150 is used to expand the urethral diameter and the extra-urethral implant 1100 is used to maintain such expanded diameter. By expanding the deployment site, the extra-urethral implant 1100 has less diameter change post deployment. Reduced diameter change post deployment can allow for a higher degree of control over the coil trajectory. FIG. 14A shows the delivery system expanded distal to the deployment site and then moved proximally to force the distal end of extra-urethral implant 1100 into the urethral wall before the rest of the implant. By rotating the implant 1100 using members of 1180 while simultaneously pulling delivery system 1150 approximately and/or further expanding delivery system 1150, extra-urethral implant 1100 can be deployed into the peri-urethral space, as depicted in FIGS. 14B and 14C.

Figure 15A:
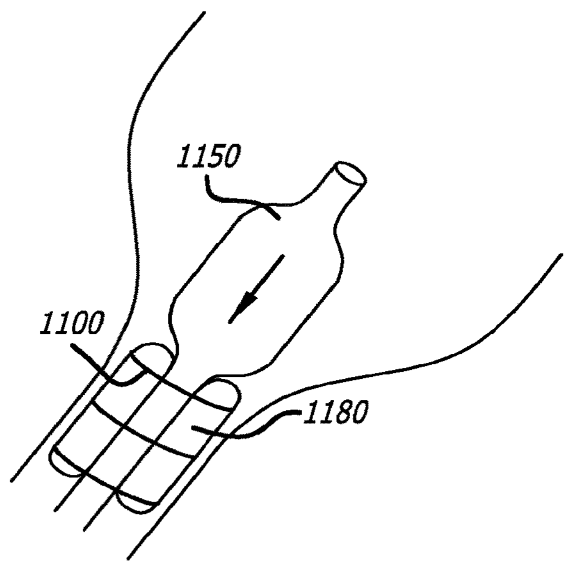
FIGS. 15A through 15C illustrate views of an embodiment in which the implant is placed using an expanding delivery member that is expanded within the bladder.
Figure 15B:
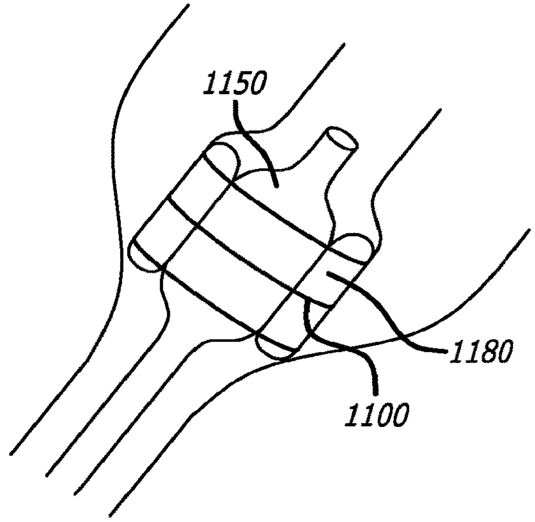
Figure 15C:
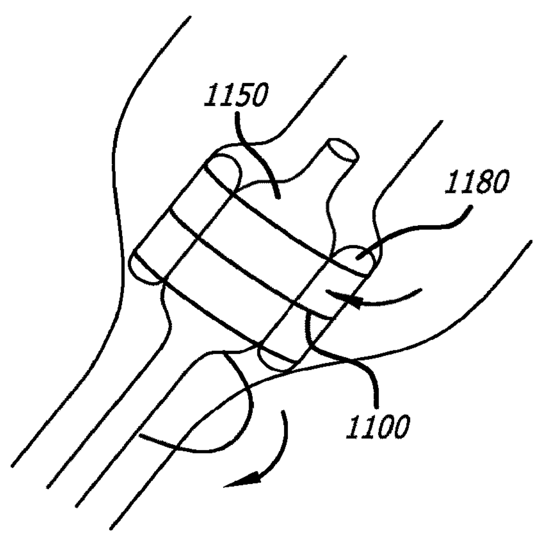
Figure 16:
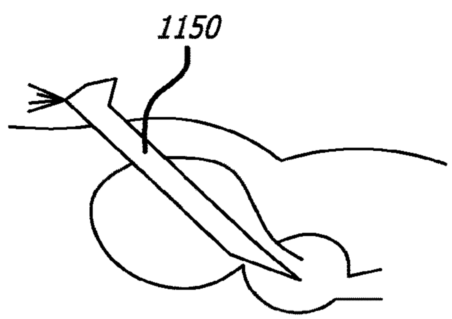
FIG. 16 illustrates a view of a supra pubic implant delivery method according to an embodiment.

In yet another embodiment depicted in FIGS. 15A through 15C, the delivery of the extra-urethral implant 1100 could be from the bladder into the prostatic urethra. In this embodiment, the very large space of the bladder can be used advantageously to position and deliver the extra-urethral implant. The delivery process is similar to that depicted in the embodiment of FIGS. 14A through 14C. In both of these embodiments, a combination of expansion, translation, and direction of rotation works to deliver the extra-urethral implant at the desired location and diameter. Further, access could be suprapubic and into the bladder as depicted in FIG. 16. Such a delivery route can give the operator more control for delivery in the ability to avoid expanding the delivery system in situ.

Figure 17A:
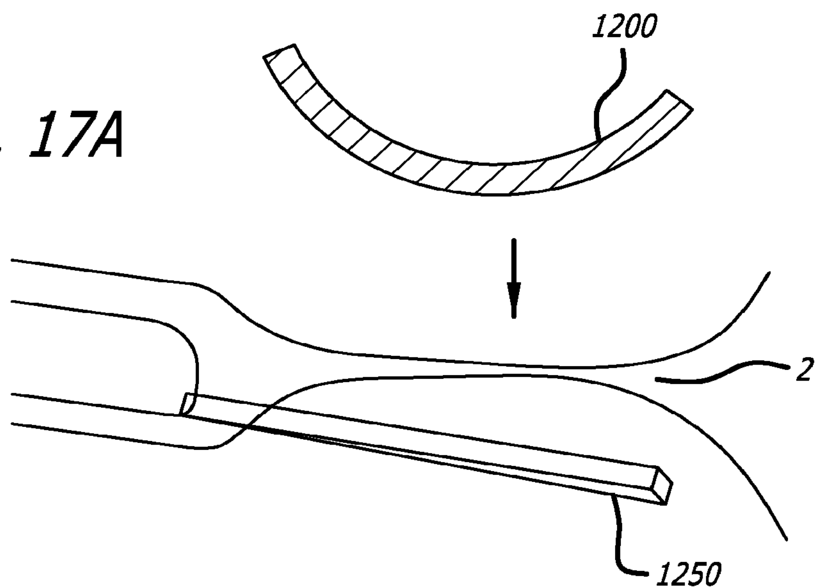
FIGS. 17A through 17C illustrative views of an arcuate implant and its delivery method according to an embodiment.
Figure 17B:
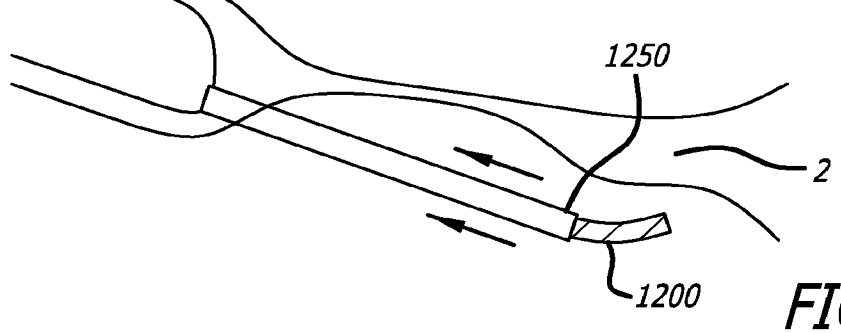
Figure 17C:
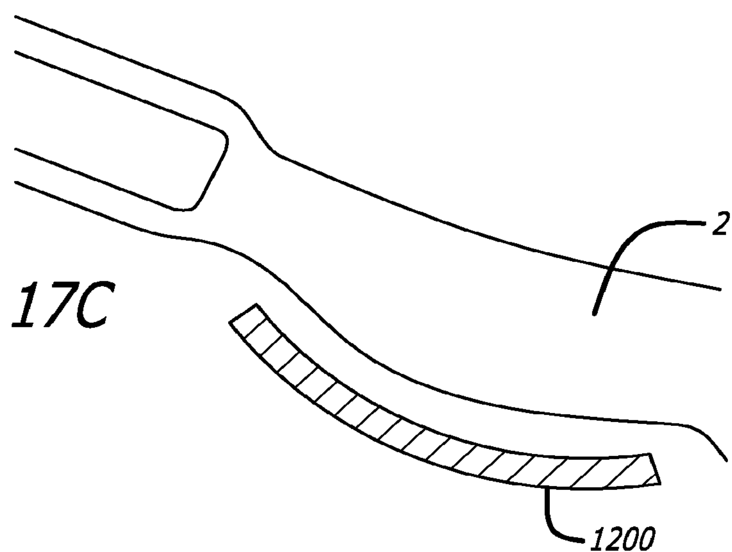

FIGS. 17A through 17C illustrate an arcuate extra-urethral implant 1200 being positioned in the peri-urethral space to enlarge the urethral lumen. The extra-urethral implant 1200 is carried within deployment tool 1250. As with other embodiments described herein, the deployment tool 1250 cuts into the peri-urethral space and the implant 1200 is advanced with respect to the deployment tool 1250. While within the deployment tool 1250, the extra urethral implant 1200 is in a substantially straight configuration. Upon deployment the extra-urethral implant 1200 can assume an arcuate configuration that helps enlarge the urethral lumen. As with other embodiments described herein, multiple implants can be positioned along the length of the prostatic urethra to achieve the desired level of enlargement.

Recalling the balance between the strength and stiffness needed to penetrate tissue and the flexibility and conformability needed to avoid damaging tissue in a chronic implant environment, other two-stage processes can be used. For example, in some subjects the tissue in the peri-urethral space can be made more mechanically resilient by a denaturing process. That is, the tissue in the peri-urethral space can be exposed to conditions that will "toughen" the tissue. Such conditions include, but are not limited to, exposure to radiofrequency heating, chemical agents, biological agents, laser energy, microwave energy, low temperatures, or equivalent means of altering the mechanical properties of tissue to cross-link portions of the tissue or otherwise stiffen the tissue. In these embodiments, the first stage can include exposure to such conditions prior to, during, or after a cutting/penetration step. Alternatively, the tissue-toughening conditions can be the first stage, and the second stage can be implantation of a self-cutting extra-urethral implant. This two-stage tissue denaturing, toughening, and/or stiffening process can be used with any of the embodiments disclosed herein or their equivalents.

Referring again to the balance between strength and stiffness needed to penetrate tissue and the flexibility and conformability needed to avoid damaging tissue in a chronic implant environment, the surface of an extra-urethral implant can be configured to enhance the mechanical coupling between the peri-urethral tissue and the implant. The peri-urethral space may contain predominantly glandular tissue that has low mechanical resilience. That is, the glandular tissue is significantly less stiff than the implant. This large mismatch in mechanical properties can be reduced by configuring the surface of the extra-urethral implant. Texture or surface features can increase the surface area contact between the implant and the prostatic tissue. Increased contact area increases the strength of the contact between the implant and the prostatic tissue. Thus, this embodiment helps overcome the mechanical mismatch between the soft, spongy prostatic tissue and the extra-urethral implant.

Figure 18:
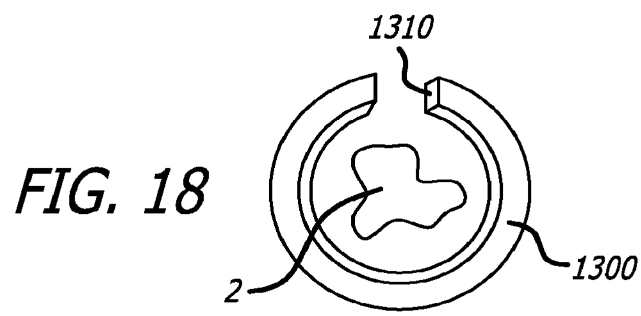
FIG. 18 illustrates a view of a self-cutting ring-type implant according to an embodiment.

FIG. 18 depicts another embodiment of an extra-urethral implant 1300, which may be implanted by inserting the implant 1300 around a lumen, moving it circumferentially around the lumen using a sharp leading edge 1310 to penetrate tissue.

Figure 19:
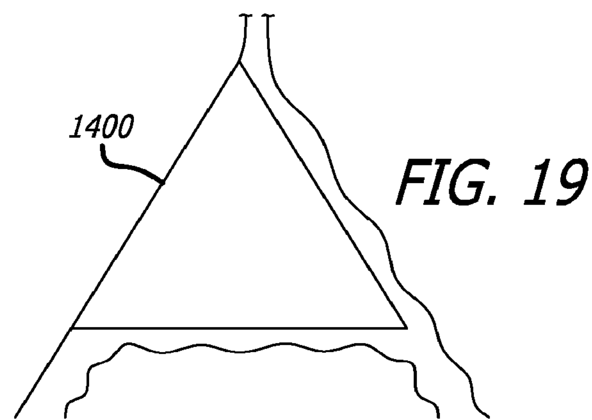
FIG. 19 illustrates a view of a triangular implant according to an embodiment.

In the embodiment depicted in FIG. 19 a circumferential implant is modeled after the shape of an obstructed urethra, for instance in a triangular shape, and inserted into extra-urethral tissue. This non-circular shape can address the challenge of displacing prostatic tissue in an anatomically-tolerable way to limit migration and provide long-term implant positional stability.

Figure 20:
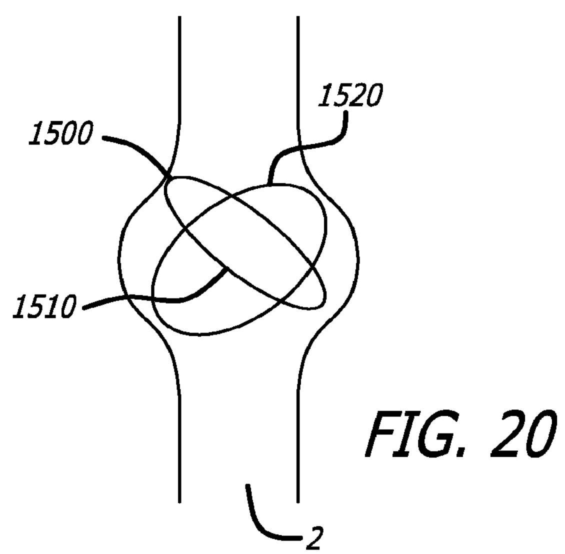
FIG. 20 illustrates a view of an implant consisting of nested rings according to an embodiment.

In the embodiment depicted in FIG. 20, a pair of nested rings, 1510 and 1520, forms the implant 1500. The rings may be introduced in a co-planar configuration and then spread apart to widen a body lumen.

Figure 21:
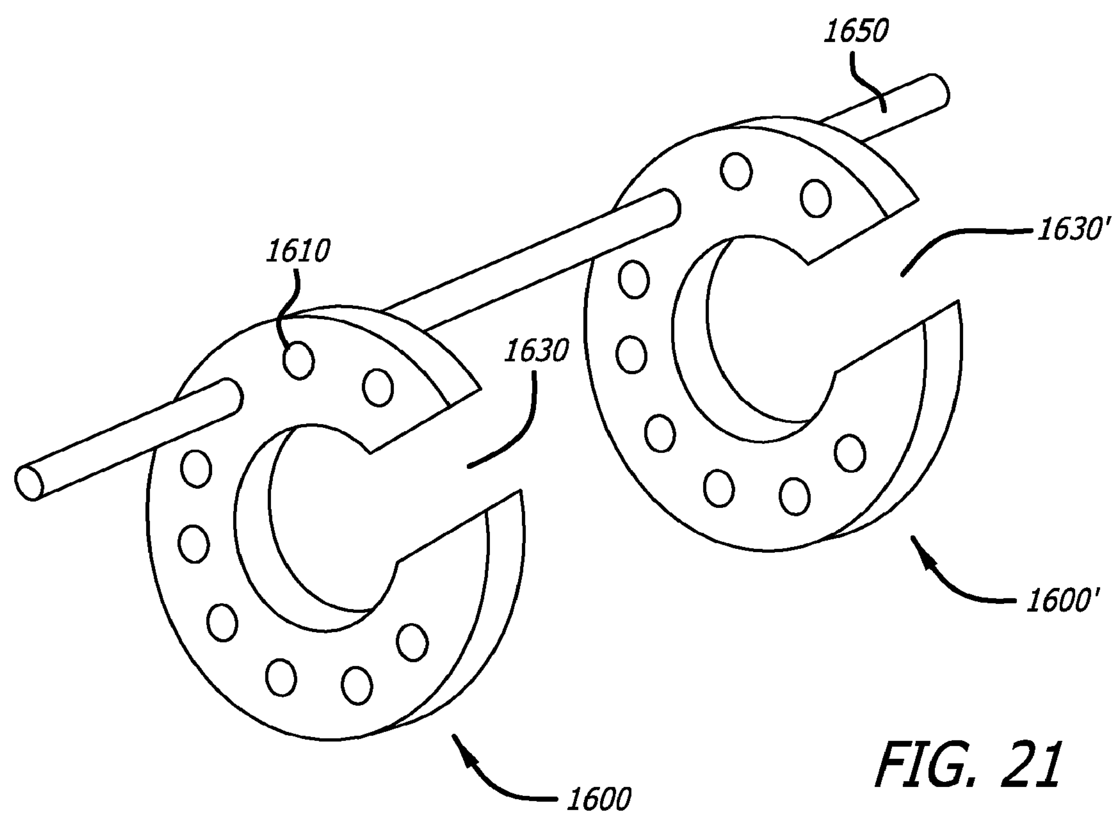
FIG. 21 illustrates a view of a series of implants connected by a flexible spine according to an embodiment.

Certain embodiments of the invention include a ring that at least partially circumscribes the urethral lumen. Effective treatment of a length of prostatic urethra may require placement of multiple rings. When multiple rings are placed, one or more of the rings may shift over time and no longer provide effective opening of the urethral lumen. FIG. 21 depicts a series of rings (1600, 1600') connected by comparatively flexible spine 1650. The spine 1650 can help prevent the rings from shifting, twisting, or otherwise moving out of position. In certain embodiments, the spine 1650 can be attached to the rings 1600, 1600' after placement of one or more of the rings. In other embodiments, the spine is connected to the rings prior to placement of the rings. FIG. 21 depicts several holes 1610 which aid in connection the spine 1650 to the rings. FIG. 21 also depicts each ring 1600, 1600' as having slot openings 1630, 1630', which aid the placement of the rings about the prostatic urethra as described in embodiments disclosed herein. Slot openings 1630 and 1630' do not have to be rotationally aligned as they are depicted in the FIG. 21 and may preferable be purposely misaligned to prevent a longitudinal segment of the prostatic urethra from being unsupported.

Certain embodiments of the invention include V-shaped extra-urethral implants. The implants are positioned such that the vertex of the V is placed outside the prostatic capsule and the legs of the V penetrate through urethral tissue and terminate in the peri-urethral space. Since the vertex is placed outside the comparatively stiffer prostatic capsule, the vertex is anchored more than it would be if it was placed within the softer tissue of the prostate gland. With the vertex placed and the prostatic capsule acting like a fulcrum, the legs of the V spread to open the angle of the V and enlarge the portion of the prostatic urethra adjacent the legs of the V. The legs can be inelastically deformed when spread by a delivery tool, such as an expanding member. Or, the legs may be compressed together during implantation and then spread when released by a delivery tool.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art.

We claim:

1. A method for treatment of a lumen of a urethra, comprising:

accessing the lumen of the urethra with a delivery device configured to carry and deliver an implant, wherein the implant comprises two rings connected by a single flexible spine oriented in a longitudinal direction of the urethra, each of the rings having a non-circular cross-sectional shape, and wherein the delivery device comprises a lock mechanism connecting a distal end portion of the delivery device and a proximal end portion of the implant;

placing the implant at a desired location within the lumen of the urethra; and releasing the implant from the delivery device via the lock mechanism, which comprises at least two opposing surfaces configured to hold a longitudinally oriented portion of the implant between the surfaces.

2. The method of claim 1, wherein the delivery device further comprises a pusher configured to deliver the implant from the delivery device to the location within the lumen of the urethra.

3. The method of claim 1, wherein the implant is configured to have a first configuration and a second configuration.

4. The method of claim 3, wherein the first configuration is a constrained configuration and the second configuration is an expanded configuration.

5. The method of claim 4, wherein the implant is configured to provide an outward radial force on the urethra in the expanded configuration.

6. The method of claim 3, wherein the implant self-expands from the first configuration to the second configuration.

7. The method of claim 3, wherein the delivery device causes the implant to change from the first configuration to the second configuration as the implant is placed at the desired location within the lumen of the urethra.

8. The method of claim 3, wherein the implant is configured to provide an outward radial force on the urethra in the second configuration.

9. The method of claim 1, wherein the implant is configured to provide an outward radial force on the urethra.

10. The method of claim 1, wherein the non-circular cross-sectional shape of each of the rings is a semi-circular shape.

11. The method of claim 1, wherein desired location within the lumen of the urethra is a portion of a prostatic urethra.

12. A method for treatment of a lumen of a urethra, comprising:

accessing the lumen of the urethra with a delivery device configured to carry and deliver an implant, wherein the implant comprises two rings connected by a single flexible spine oriented in a longitudinal direction of the urethra, each of the rings having a non-circular cross-sectional shape, and wherein the delivery device comprises a lock mechanism connecting a distal end portion of the delivery device and a proximal end portion of the implant and a pusher mechanism configured to push the implant from the delivery device;

placing the implant at a desired location within the lumen of the urethra via the pusher mechanism; and releasing the implant from the delivery device via the lock mechanism, which comprises at least two opposing surfaces configured to hold a longitudinally oriented portion of the implant between the surfaces.

13. The method of claim 12, wherein the implant is configured to have a first configuration and a second configuration.

14. The method of claim 13, wherein the first configuration is a constrained configuration and the second configuration is an expanded configuration.

15. The method of claim 13, wherein the implant self-expands from the first configuration to the second configuration.

16. The method of claim 13, wherein the delivery device causes the implant to change from the first configuration to the second configuration as the implant is placed at the desired location within the lumen of the urethra.

17. The method of claim 13, wherein the implant is configured to provide an outward radial force on the urethra in the second configuration.

18. The method of claim 14, wherein the implant is configured to provide an outward radial force on the urethra in the expanded configuration.

19. The method of claim 12, wherein the implant is configured to provide an outward radial force on the urethra.

20. The method of claim 12, wherein the non-circular cross-sectional shape of each of the rings is a semi-circular shape.

* * * * *